US009795375B2

(12) United States Patent
Lore et al.

(10) Patent No.: US 9,795,375 B2
(45) Date of Patent: Oct. 24, 2017

(54) APPARATUS AND METHOD FOR SUTURING A TISSUE

(71) Applicant: Anchora Medical Ltd., Yokneam (IL)

(72) Inventors: Avraham Rami Lore, Kiryat Tiv'on (IL); Yuval Gonen, Kiryat Tiv'on (IL)

(73) Assignee: ANCHORA MEDICAL LTD., Yokneam (IL)

( * ) Notice: Subject to any disclaimer, the term of this patent is extended or adjusted under 35 U.S.C. 154(b) by 0 days.

(21) Appl. No.: 15/091,613

(22) Filed: Apr. 6, 2016

(65) Prior Publication Data

US 2016/0242761 A1 Aug. 25, 2016

Related U.S. Application Data

(63) Continuation of application No. PCT/IL2015/050599, filed on Jun. 14, 2015.
(Continued)

(51) Int. Cl.
*A61B 17/04* (2006.01)
*A61B 17/06* (2006.01)
*A61B 17/00* (2006.01)

(52) U.S. Cl.
CPC ...... *A61B 17/0401* (2013.01); *A61B 17/0467* (2013.01); *A61B 17/0469* (2013.01); *A61B 17/0491* (2013.01); *A61B 17/06066* (2013.01); *A61B 2017/00004* (2013.01); *A61B 2017/0409* (2013.01); *A61B 2017/0414* (2013.01);
(Continued)

(58) Field of Classification Search
CPC ............ A61B 17/0401; A61B 17/0469; A61B 17/0467; A61B 2017/06052; A61B 2017/0409; A61B 17/06066; A61B 17/0491; A61B 2017/0417; A61B 2017/0437; A61B 2017/0456; A61B 2017/0464; A61B 2017/0427; A61B 2017/0454; A61B 2017/0414; A61B 2017/0412; A61B 2017/0429;
(Continued)

(56) References Cited

U.S. PATENT DOCUMENTS 4,823,794 A * 4/1989 Pierce ................ A61B 17/0401
606/232
5,041,129 A * 8/1991 Hayhurst ........... A61B 17/0401
606/139
(Continued)

FOREIGN PATENT DOCUMENTS

EP 2581046 A1 4/2013
FR 2731610 A1 9/1996
(Continued)

*Primary Examiner* — Jing Ou
(74) *Attorney, Agent, or Firm* — The Roy Gross Law Firm, LLC; Roy Gross

(57) ABSTRACT

Embodiments of the invention are related to an apparatus for suturing a tissue. The apparatus includes an outer tube, a thread threaded in the outer tube and at least one anchoring element located inside the outer tube and configured to be inserted into the tissue from an outlet end of the outer tube. The outer tube is configured to freely accommodate the thread and the at least one anchoring element, and the anchoring element includes a body adapted to be threaded on the thread and having at least locking element for locking the thread to the anchoring element.

9 Claims, 19 Drawing Sheets

Related U.S. Application Data

(60) Provisional application No. 62/012,363, filed on Jun. 15, 2014.

(52) U.S. Cl.
CPC ............... *A61B 2017/0417* (2013.01); *A61B 2017/0427* (2013.01); *A61B 2017/0437* (2013.01); *A61B 2017/0454* (2013.01); *A61B 2017/0456* (2013.01); *A61B 2017/0458* (2013.01); *A61B 2017/0464* (2013.01); *A61B 2017/061* (2013.01); *A61B 2017/06052* (2013.01)

(58) Field of Classification Search
CPC .... A61B 2017/061; A61B 2017/00004; A61B 2017/0458
See application file for complete search history.

(56) References Cited

U.S. PATENT DOCUMENTS

| | | | |
|---|---|---|---|
| 5,782,866 A | 7/1998 | Wenstrom, Jr. | |
| 5,791,022 A * | 8/1998 | Bohman | F16G 11/10 24/115 R |
| 6,007,566 A | 12/1999 | Wenstrom, Jr. | |
| 6,966,916 B2 | 11/2005 | Kumar | |
| 7,674,275 B2 | 3/2010 | Martin et al. | |
| 7,815,662 B2 | 10/2010 | Spivey et al. | |
| 8,317,679 B2 | 11/2012 | Surti | |
| 8,376,932 B2 | 2/2013 | Hashiba et al. | |
| 8,551,139 B2 | 10/2013 | Surti et al. | |
| 8,771,314 B2 | 7/2014 | Crombie et al. | |
| 9,198,648 B2 | 12/2015 | Crombie et al. | |
| 2002/0019649 A1 * | 2/2002 | Sikora | A61B 17/0401 606/232 |
| 2002/0188301 A1 * | 12/2002 | Dallara | A61B 17/064 606/104 |
| 2003/0120287 A1 * | 6/2003 | Gross | A61B 17/0467 606/148 |
| 2004/0122474 A1 * | 6/2004 | Gellman | A61B 17/0401 606/232 |
| 2004/0210241 A1 | 10/2004 | James et al. | |
| 2006/0178680 A1 * | 8/2006 | Nelson | A61B 17/0401 606/139 |
| 2006/0293710 A1 * | 12/2006 | Foerster | A61B 17/0401 606/232 |
| 2007/0112385 A1 * | 5/2007 | Conlon | A61B 17/0401 606/232 |
| 2007/0112425 A1 * | 5/2007 | Schaller | A61B 17/00234 623/2.37 |
| 2008/0234729 A1 * | 9/2008 | Page | A61B 17/0485 606/232 |
| 2009/0082786 A1 | 3/2009 | Surti | |
| 2010/0030263 A1 * | 2/2010 | Cheng | A61B 17/0401 606/232 |
| 2010/0049212 A1 * | 2/2010 | Caborn | A61B 17/0401 606/139 |
| 2010/0057124 A1 * | 3/2010 | Triel | A61F 2/0045 606/232 |
| 2010/0121355 A1 * | 5/2010 | Gittings | A61B 17/0401 606/148 |
| 2011/0071551 A1 | 3/2011 | Singhatat et al. | |
| 2011/0172682 A1 * | 7/2011 | Brady | A61B 17/0401 606/144 |
| 2015/0250470 A1 * | 9/2015 | Vargas | A61B 17/0401 606/232 |

FOREIGN PATENT DOCUMENTS

| | | |
|---|---|---|
| WO | 2011010011 A1 | 1/2011 |
| WO | 2013114347 A1 | 8/2013 |
| WO | 2013131023 A2 | 9/2013 |
| WO | 2014033692 A2 | 3/2014 |

\* cited by examiner

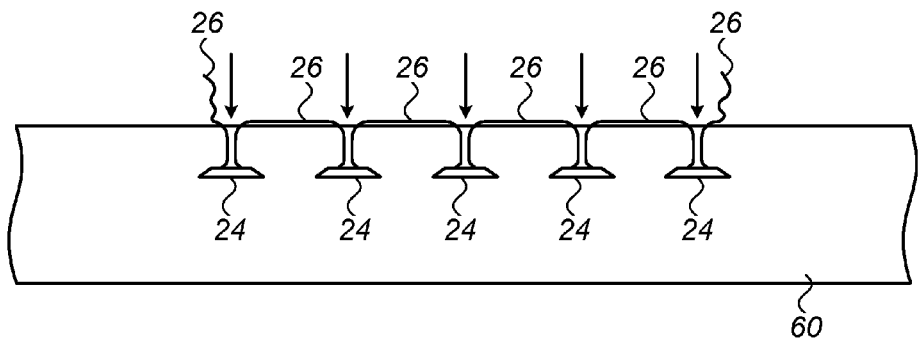
*FIG. 5A*
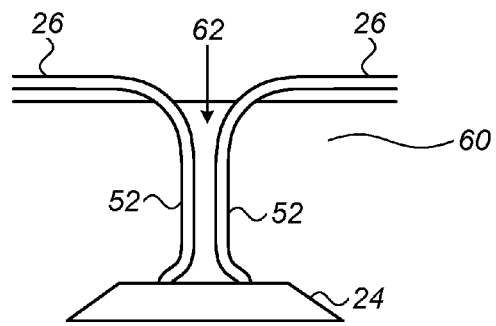
*FIG. 5B*
*FIG. 5C*
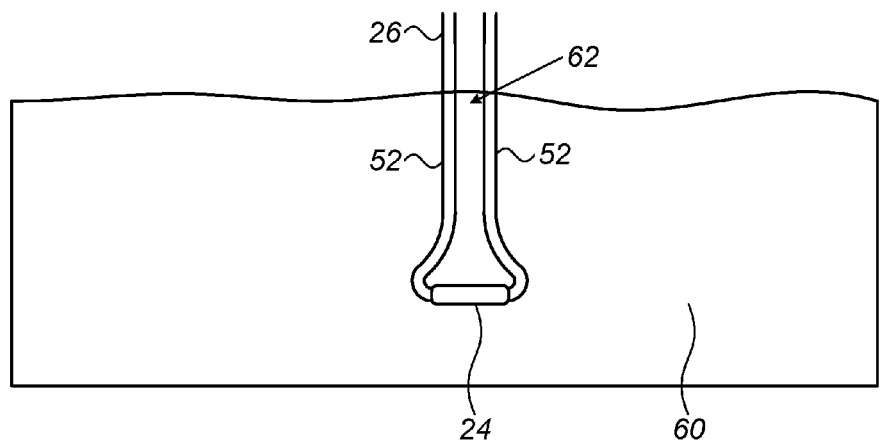

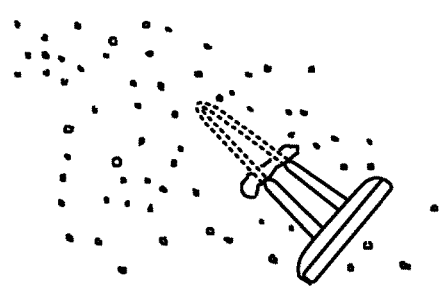
FIG. 8B
FIG. 8C
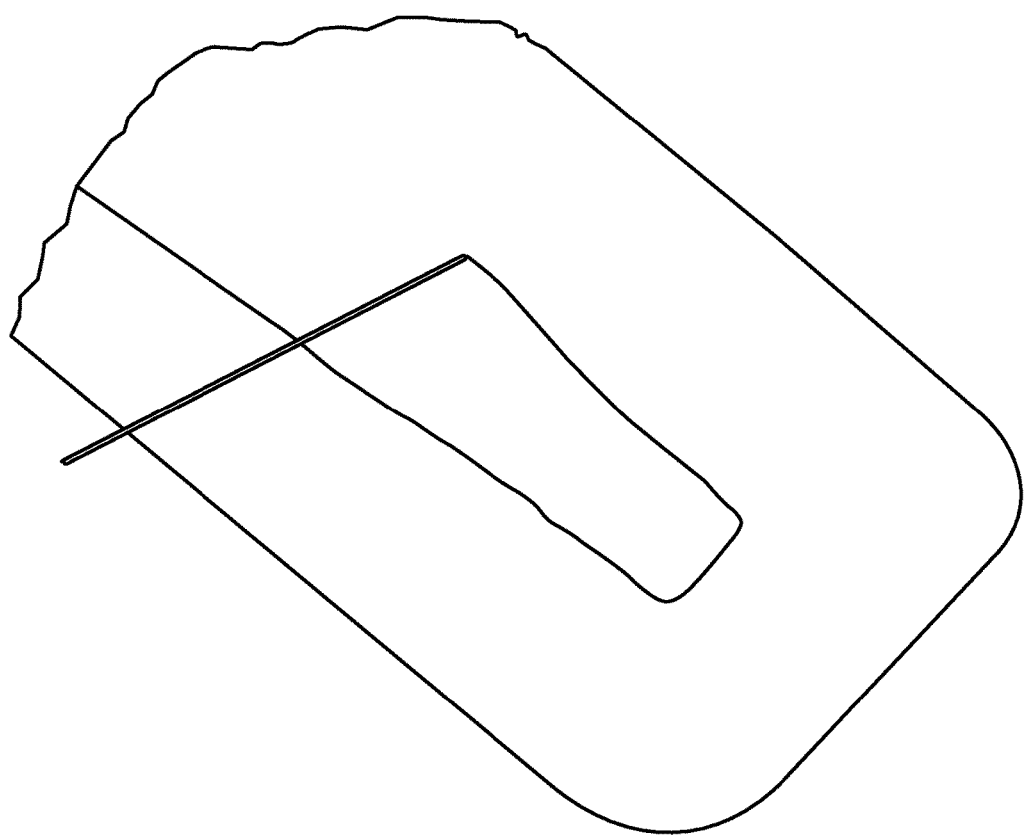

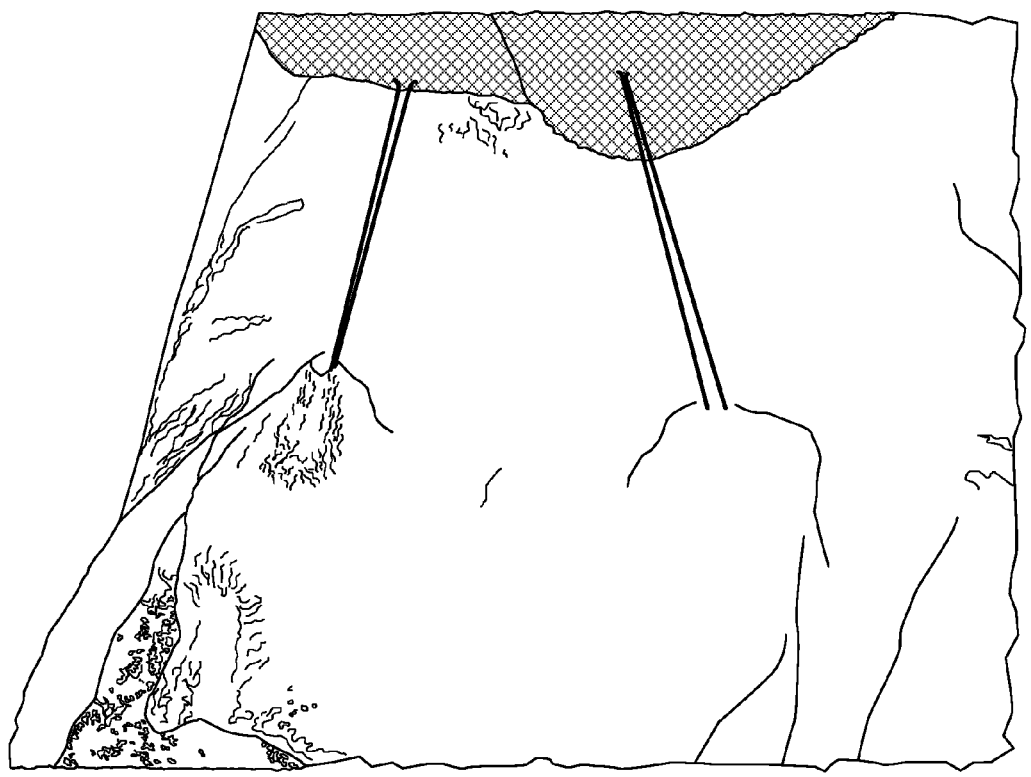
FIG. 9A
FIG. 9B
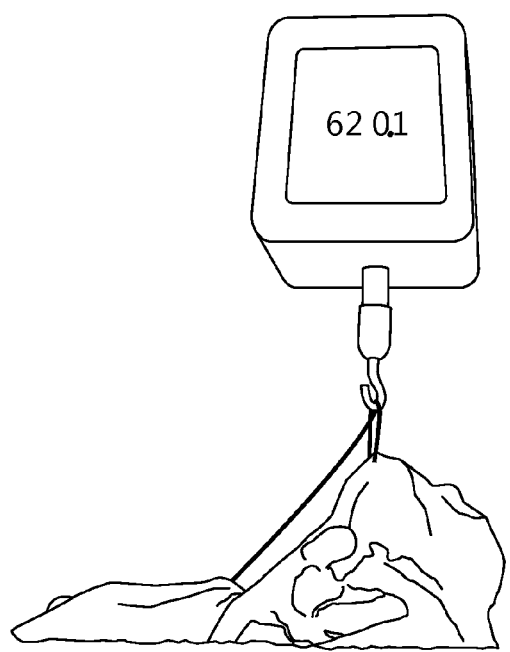

APPARATUS AND METHOD FOR SUTURING A TISSUE

CROSS-REFERENCE TO RELATED APPLICATIONS

This application is a continuation of PCT Patent Application No. PCT/IL2015/050599, filed on Jun. 14, 2015, which claims the benefit of priority to U.S. Provisional Patent Application No. 62/012,363, filed on Jun. 15, 2014, both of which are incorporated herein by reference in their entirety.

BACKGROUND OF THE INVENTION

The present invention relates to a device for suturing tissue and, more particularly, to an apparatus and device capable of threading a continuous or single adjusted length and depth of suture through a tissue and to a method of using same to approximate, ligate, suture or fixate tissue and/or an implant such as a mesh.

Suturing remains a common approach for repair of tissues and is used for tissue approximation, ligation and fixation of tissue access sites, organs, vessels, fixation of meshes and other implants or devices and the like. Although largely dependent on the skill of the surgeon, the results obtained using a suture are highly predictable and reliable.

Alternatives to suturing developed over the years such as staples, fasteners (tackers), anchors and tissue adhesives, have gained varying degrees of acceptance and are used for tissue repair in both open and minimally invasive procedures. Nonetheless, suturing remains ubiquitous in surgical repair due to availability of a wide variety of suturing kits at relatively low costs and the mechanical advantages afforded by suturing.

Thus, suture remains a mainstay of surgical repair however, it is not without disadvantages. Placing a number of stitches can be tiring and time-consuming which can lead to suturing errors that can compromise the integrity of repair. In addition, manipulation of a suture needle as well as access to the suturing location can be difficult especially in minimally invasive surgery due to the nature of the minimally invasive surgery and/or the limited anatomical space around the target tissues, while tying knots with a desired amount of tension requires precise manipulation of the suture ends further complicating and slowing open, and in particular, minimally-invasive surgeries. In fact, for many procedures the time spent suturing may be significantly greater than the time spent treating the underlying target tissues.

Although tissue stapling devices and adhesives as well as devices which employ a combination of anchors and sutures can traverse these limitations of suturing by enabling rapid ligation of tissue, the tissue ligation/fixation created thereby is oftentimes less reliable or does not involve easy access and large number of sutures.

Thus, there remains a need for a device capable of ligating/fixating tissues rapidly and reliably while being operable within a confined anatomical space through a minimally invasive approach.

SUMMARY OF THE INVENTION

Some embodiments of the invention may be related to an apparatus for suturing a tissue. The apparatus may include an outer tube, a thread threaded in the outer tube and at least one anchoring element located inside the outer tube and configured to be inserted into the tissue from an outlet end of the outer tube. The outer tube may be configured to freely accommodate the thread and the at least one anchoring element, and the anchoring element may include a central elongated body adapted to be threaded on the thread and having at least one recess, the recess having a wide end and a narrow end, the narrow end is for gripping the thread during suturing of the tissue.

Some additional embodiments of the invention may be related to an insertion device for inserting a thread and one or more anchoring elements into a tissue. The insertion device may include: an outer tube, a thread guide tube for guiding a thread inserted in the thread guide tube. The outer tube may be configured to freely accommodate the thread guide tube and one or more anchoring elements threaded on the thread guide tube such that each anchoring element can slid along the outer tube to be exit from an outlet end of the outer tube.

Some embodiments of the present invention may include an anchoring element for anchoring a suture in a tissue including a central elongated body adapted to be threaded on a thread and having at least one recess, the recess having a wide end and a narrow end, the narrow end is to grip the thread during anchoring.

Some embodiments of the invention may be related to a method of suturing a tissue. The method may include piercing the tissue while inserting to the tissue an apparatus for suturing, the apparatus may include an outer tube, a thread inserted in the outer tube and at least one anchoring element located inside the outer tube, threaded on the thread and configured to be inserted into the tissue from an outlet end of the outer tube, wherein the anchoring element comprises a central elongated body adapted to be threaded on the thread and having at least one recess, the recess having a wide end and a narrow end, the narrow end to gripping the thread during suturing of the tissue. The method may further include advancing the at least one anchoring element towards the outlet end of the outer tube to cause the at least one anchoring element to exit from the outlet end of the outer tube into the tissue such that the at least one anchoring element is anchored in the tissue and threaded on the thread and causing the thread to be gripped at the narrow end of the recess of the anchoring element.

Some embodiments of the present invention may include a device including: (a) an elongated shaft; (b) a plurality of anchor elements and a suture co-axially disposed along the elongated shaft; and (c) a handle attached to a proximal end of the shaft, the handle being for actuating release of an anchor element attached to a portion of the suture from a distal end of the shaft.

According to further embodiments of the invention described below, the anchor element may be hollow with the portion of the suture threaded there-through.

In some embodiments, the plurality of anchor elements may be concentric with the suture.

In some embodiments, the plurality of anchor elements and the suture may be disposed within a lumen of the elongated shaft.

In some embodiments, the device may further include at least one of: mechanism for advancing the anchor element and the suture in a direction of the distal end.

In some embodiments, the anchor element may attach and/or lock to the portion of the suture when the anchor element is released from the distal end.

In some embodiments, a wall of the anchor element may include at least one longitudinal slot for trapping the portion of the suture when the anchor element is advanced in the direction of the distal end.

In some embodiments, the portion of the suture may loop through the anchor element.

In some embodiments, the device may be capable of positioning a plurality of contiguous loops of the suture each may have a dedicated anchor element threaded thereon through a tissue wall.

In some embodiments, a length of the portion of the suture released from the distal end may be adjustable.

In some embodiments, the distal end of the shaft may be configured for piercing through a tissue.

In some embodiments, the anchor element may be configured for piercing through a tissue.

In some embodiments, the device may further include a first tube disposed within the lumen, wherein the plurality of anchor elements may be disposed around the first tube and the suture may be disposed within the first tube.

According to still further embodiments, the device may further include a second tube disposed within the lumen and around the plurality of anchors.

According to still further embodiments, the second tube may include a tissue piercing distal end.

According to still further embodiments, the device further may include a mechanism for advancing the second tube and the anchor element in a direction of the distal end of the shaft.

In some embodiments, the device may further include a suture cutting element in or on the shaft.

In some embodiments, the mechanism for advancing the second tube and the anchor element may be actuatable from the handle.

In some embodiments, the mechanism for advancing the second tube and the anchor element may be capable of retracting the second tube.

In some embodiments, the suture cutting element may be actuatable from the handle.

Embodiments of the invention may be directed to a tissue suturing device that may include: (a) an elongated hollow shaft surrounding a first co-axial tube and a second coaxial tube having a tissue piercing end; (b) a suture disposed within the first tube; (c) a plurality of anchoring elements disposed around the first tube and within the second tube; and (d) a handle attached to a proximal end of the shaft, the handle may be for actuating a mechanism for advancing and retracting the second tube and an anchor element in a direction of a distal end of the hollow shaft so as may enable the anchor element to grab the suture and form a loop of the suture attached to the anchor element when released the distal end of the shaft.

Some embodiments of the present invention may be related to a method of suturing tissue. Embodiments of the method may include: (a) providing a tissue suturing device having an elongated shaft and plurality of anchor elements and a suture co-axially disposed along the elongated shaft; (b) positioning a distal end of the elongated shaft through an opening in the tissue; and (c) actuating release of an anchor element attached to a loop of the suture from the distal end of the shaft.

In some embodiments, the method may further include (d) retracting the distal end of the elongated shaft from the opening in the tissue to thereby juxtapose the anchor element against an internal surface of the tissue and pull strands of the suture loop out of the opening.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 5A is an illustration of several contiguous suture loops with attached anchoring elements positioned through a tissue according to some embodiments of the invention;

FIG. 5B is an illustration of magnified view of one thread loop and attached anchoring element positioned through the tissue according to some embodiments of the invention;

FIG. 5C is an illustration of a thread loop with attached bio-absorbable anchoring element (shown partially absorbed) positioned in a tissue according to some embodiments of the invention;

FIGS. 8B-8C are photographs of a delivery of an anchored suture through a foam board (FIG. 8B) and the running stitch created by sequentially delivering several anchoring elements from a prototype assembled from the components shown in FIG. 8a, according to some embodiments of the invention;

FIGS. 9A-9B are photographs of two anchoring sites created using the apparatus for suturing a tissue (FIG. 9A) and testing of the load capacity of a single anchoring site (FIG. 9B), according to some embodiments of the invention;

Figure 1:
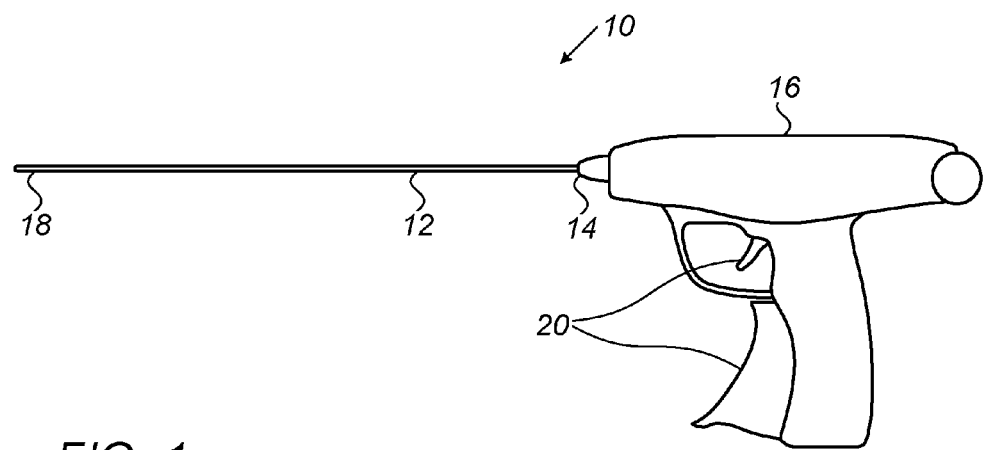
FIG. 1 is an illustration of a side view of an exemplary apparatus for suturing a tissue according to some embodiments of the present invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Some embodiments of the present invention may be related to an apparatus for suturing or fixating a tissue. The tissue may soft or hard tissue. Such apparatus may include three (3) main components, a thread, one or more anchoring elements for anchoring the thread in the tissue and an insertion device for inserting the thread and anchoring elements into the tissue. Such a tissue suturing device which may be used to approximate, suture, ligate, and fixate tissue and an implant such as a mesh. Specifically, the embodiments of the invention may be used for repair of tissue defects, anastomosis of vessels or organs, suturing of access sites, anchoring or fixating soft or hard tissue, fixating meshes or other implants or devices to a tissue, closing natural or artificial tissue openings, modifying anatomical spaces, lifting, stretching, pulling or retracting tissues or organs using open or minimally invasive approaches.

The principles and operation of the embodiments of the invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Devices for ligating and fixating tissues which may be used via minimally invasive approaches are well known in the art, such devices typically utilize sutures, mechanical fasteners/anchors or a combination thereof.

A suturing system or suturing device according to embodiments of the invention may be capable of positioning and anchoring one or more separated or contiguous loops of suture with or without adjustable suture lengths and with or without adjustable suture depth through a tissue while traversing the need for a tissue suturing head that spans the tissue wall or for a curved needle capable of threading in and out of a tissue wall.

In some embodiments, a tissue suturing device may be capable of approximating, ligating and fixating tissues and/or implants such as meshes and the like and may be used in both open and minimally invasive surgeries.

Embodiments of such device may include: a rigid or flexible elongated device body (also referred to herein as "shaft" or "an insertion device") which may be with or without a distal curved section towards its outlet and a plurality of anchoring elements and a suture co-axially disposed along the shaft. As is further described herein, the anchoring elements and suture may be disposed on the shaft (e.g. in a guide rail running along the length of the shaft) or within the shaft (e.g. in a lumen running along the length of shaft). The suture may also be arranged on the shaft outlet dividing the outlet area. In any case, the anchoring elements and sutures are arranged co-axially (i.e. the suture and anchoring elements may be arranged along the length of the shaft) and preferably concentrically. The anchoring elements may be arranged such that they assume the same rotational position along the shaft, or alternatively, the anchoring elements may be arranged with rotational offset therebetween.

As used herein, the term "suture" refers to any non-rigid elongated element that can be looped through a tissue. A suture may be made from a thread that may be fabricated from a natural or synthetic polymer, an alloy or any other bio compatible material, and may include a single filament or several braided or twisted filaments. The thread may be of any diameter, shape (e.g. with edges), length and pull strength. The thread may be permanent or degradable or mixed (partly degradable and partly permanent) depending on the tissue sutures and the site of suturing. Examples of threads suitable for use with embodiments of the present invention may include absorbable threads that may result in absorbable sutures fabricated from, for example, catgut, polyglycolic acid, polylactic acid, polydioxanone, or caprolactone. Non-absorbable threads to form permanent sutures that may be used with embodiments of the present invention may be fabricated from, for example, silk, nylon, polypropylene, or polyester.

As used herein the phrase "anchoring elements" (or simply anchor) refers to any element having a length which is preferably greater than a diameter thereof with a diameter suitable for delivery through a hole in a tissue (self-generated or pre-generated) and a length suitable for abutting the hole and anchoring thereagainst. As is further described hereinunder, the anchoring elements may be configured such that it can slide on a thread or a suture and attach thereto.

Although anchoring may be provided by contact between the anchor and inner tissue wall, additional anchoring features may be used to increase such anchoring. For example, the anchoring element body can include a roughened surface, deployable tabs or barbs or fin or any other element or elements that may enhance tissue fixation via adhesion, tissue penetration or tissue pinching.

Embodiments of a device of the present invention may further include a handle which may be attached to the proximal end of the shaft (the outer tube). The handle may be permanently attached to the shaft or inner tubes or removably attached thereto. The latter case may enable the use of several handle types with one shaft and/or reuse of the handle or use of one handle with several shafts.

The handle may actuate release of one or more anchoring elements attached to a portion of a thread from the distal end of the shaft. As is further described hereinunder, actuation of the anchoring elements-thread release mechanism (via the handle), may deliver an anchoring element attached to a loop of thread (e.g., for forming a suture) through an opening in tissue wall. The anchoring element may abut the internal surface of the tissue and may anchor the loop of thread through the tissue opening.

Embodiments of an exemplary device according to the invention may carry a single continuous strand of thread disposed co-axially (e.g., concentrically) with a plurality of suture elements along the length of the shaft. Such exemplary device may be used to deliver several contiguous loops of the thread (while enabling adjustment of suture length, depth and tension) without having to access both sides of the tissue. In other words, embodiments of the present device may position a running stitch through a tissue wall by approaching a tissue surface and without having to access both sides of the tissue wall and/or without necessitating threading of a needle in and out of tissue. This embodiment of the present device may particularly be advantageous in cases where a surgical mesh is used in hernia defect repair and/or where the hernia defect is sutured. A hernia mesh is typically fixated to an abdominal wall via trans-facial suturing by looping a suture in and out of the abdominal wall. Such suturing is time consuming, associated with postoperative pain and infections and requires a high level of skill since the stability of the mesh depends on the quality of suturing. Post the trans-facial fixation, the mesh is adhered to the tissue usually with a tacking device. The tacks protrude into the abdominal cavity and may cause tissue adhesions. In addition, numerous tacks are needed to secure the mesh which increases the likelihood of damaging nerve tissue and inducing postoperative pain. Tacks may not hold the tension and may detach from the tissue specially if opposing the tissue in a non-vertical angle.

Referring now to the drawings, FIGS. 1-7F are illustrations of exemplary apparatus for anchoring a suture in a tissue. Embodiments of apparatus 10 may be configured to deliver of one or more anchoring element-thread loops through a tissue wall and can be used in minimally invasive procedures (endoscopic, laparoscopic) as well as open procedures.

Embodiments of apparatus 10 may include: an insertion device 12 (e.g., a shaft) having a proximal end 14 (releasable or permanently) attached to a handle 16. Device 12 may be configured to insert a thread and one or more anchoring elements into a tissue. Apparatus 10 may further include a thread 26 and at least one anchoring element 24, both illustrated in FIG. 2. Handle 16 may house a mechanism for managing the suture and for actuating tissue piercing, anchoring element-thread delivery holding and severing of the thread at distal end 18 of insertion device 12. User interface 20 of handle 16 may include controls (buttons, triggers dials) for setting the depth of tissue penetration, actuating tissue piercing, generating tension on the thread, delivering the anchoring element and attached loop of thread through the tissue and for holding and severing the thread at the end of a suturing cycle (of one or more anchoring elements). Handle 16 is described in greater detail hereinbelow with reference to FIGS. 7A-7D.

Figure 2A:
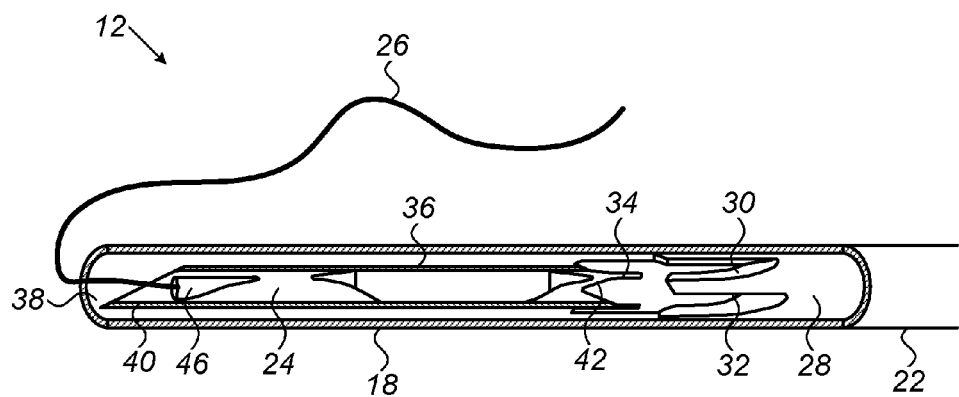
FIGS. 2A-2C are isometric illustrations of cutaway views of the distal portion of the exemplary apparatus of FIG. 1 according to some embodiments of the invention.
Figure 2B:
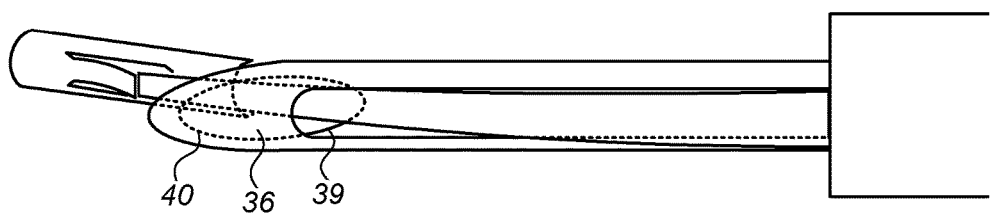
Figure 2C:
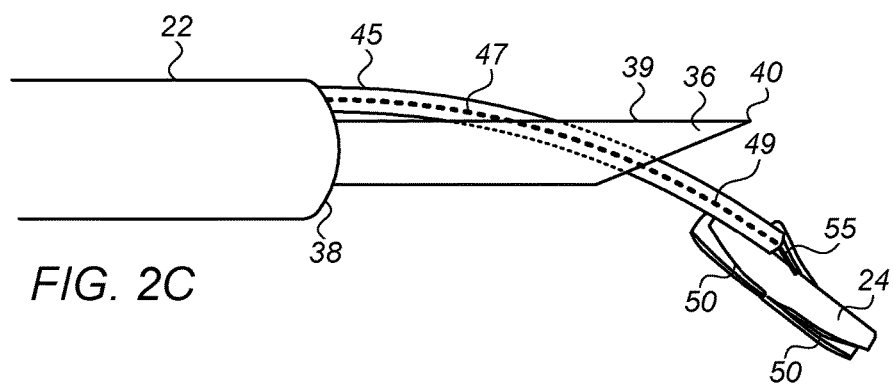

Reference is made to FIGS. 2A-2C that are illustrations of distal end 18 of apparatus 10 in greater detail. Insertion device 12 of apparatus 10 may include: an outer tube 22, a thread guide tube 46, a thread 26 threaded in thread guide tube 46 and at least one anchoring element 24 located inside outer tube 22. In some embodiments, thread 26 may be located outside of insertion device 12 (not threaded in the insertion device), such that only a small portion of the thread is guided, lead or held by distal end 18. In the exemplary embodiment shown in FIG. 2, insertion device 12 may composed of five concentrically (and optionally coaxially) arranged tubes with outer tube 22 housing four (or less) internal tubes. Outer tube 22 can be fabricated from an alloy or polymer (rigid or flexible) for example, stainless steel, cobalt chrome, Nitinol, PEEK (polyether ether ketone), carbon, composite material, reinforced plastics, Ceramics with a length of 5 mm-2000 mm or more. Outer tube 22 may have an outer diameter (OD) of 0.3 mm to 20.1 mm and an internal diameter (ID) of 0.25 mm to 20.05 mm. Outer tube 22 shown in FIGS. 2A-2C is cylindrical in shape and as such has a substantially circular cross section. However, outer tube can be provided with any external cross sectional shape including rectangular, square triangular and the like as long as the lumen thereof is shaped to accommodate the tubes carried therein.

Outer tube 22 may be configured to freely accommodate guide tube 46 (e.g., thread guide tube) and one or more anchoring elements 24 threaded on guide tube 46 such that each anchoring element 24 can slid along outer tube 22 to be exit from an outlet end 38 (e.g., the distal end) of outer tube 22. Alternatively, outer tube 22 may guide anchoring elements 24. In such embodiments, device 12 does not include guide tube 46 and anchoring elements 24 may be threaded directly on thread 26. In some embodiments, the distal end 38 of outer tube 22 may have a sharpened end adapted for piercing the tissue or blunt in order to penetrate a tissue directly (port less delivery) or it may be blunt and deliverable through a premade tissue access site (port or portless).

In some embodiments, at least a portion of thread 26 may be inserted into thread guide tube 46 to be guided along the longitudinal axis of device 12 and a second portion of the thread may be located external to device 12. The connection between the first and second portions may thread an anchoring element 24 to form a suture loop. Alternatively, both the first and second portions may be inserted into device 12, such that only a loop of thread including anchoring element 24 may exit device 12 into the tissue.

Device 12 may further include a thread severing (cutting) tube 28 which may be positioned internally to outer tube 22. Thread severing tube 28 can be fabricated from an alloy or polymer (rigid or flexible) (e.g. stainless steel, cobalt chrome, Nitinol, PEEK, carbon, composite material, reinforced plastics, ceramics) with a length of 5 mm to 2000 mm, an outer diameter (OD) of 0.3 mm to 20.1 mm and an internal diameter (ID) of 0.25 mm to 20.05 mm.

Thread severing tube 28 may include finger-like longitudinal projections 30 which are circumferentially spaced apart via cutouts 32. Projections 30 may be machined or laser cut from the tube using approaches well known in the art. Projections 30 may widen distal to proximal and may be configured as sharpened blades.

A thread trapping tube 34 may be positioned inside thread severing tube 28. Tube 34 can be fabricated from an alloy or polymer (e.g. stainless steel, cobalt chrome, Nitinol, PEEK, carbon, composite material, reinforced plastics, ceramics) with a length of 5 mm to 2000 mm, an outer diameter (OD) of 0.3 mm to 20.1 mm and an internal diameter (ID) of 0.25 mm-20.05 mm.

Figure 6A:
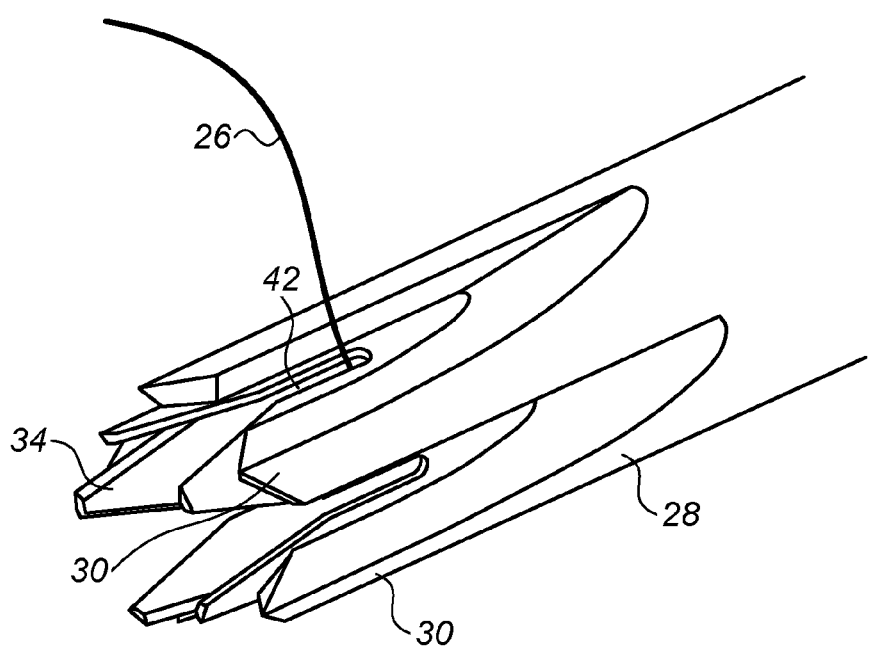
FIGS. 6A-6B are illustrations of an embodiment of a mechanism for thread holding and cutting according to some embodiments of the invention.
Figure 6B:
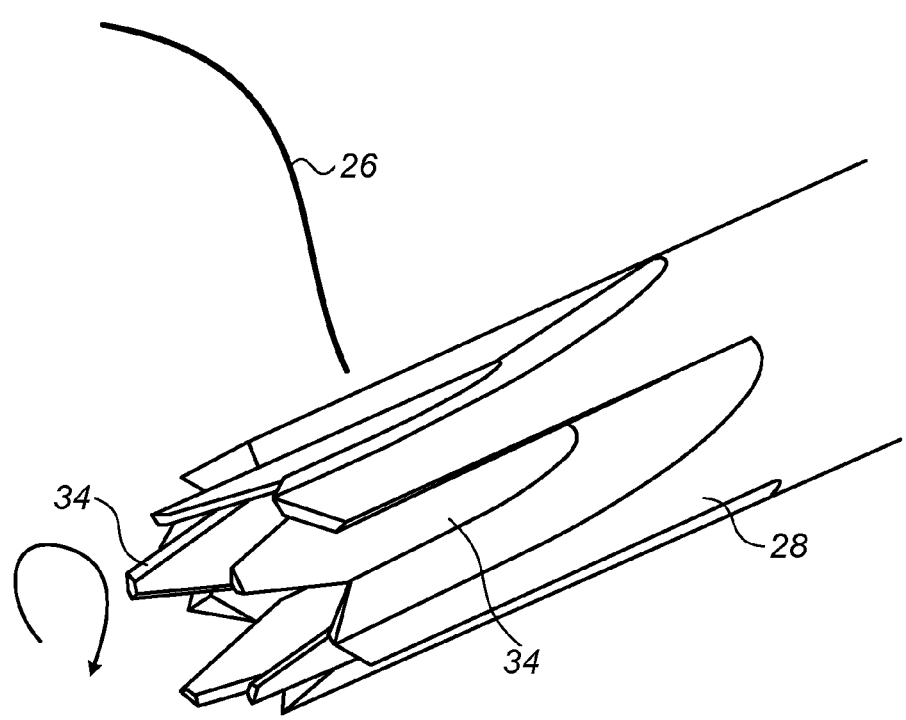

As is shown in FIGS. 6A-6B tube 34 may cooperate with projections 30 of thread severing tube 28 to sever thread 26. To enable such functionality, distal portion of tube 34 may include thread traps 42 for trapping thread 26 pulled therein. Advancement of tube 34 and thread severing tube 28 out of opening 38 (Shown in FIGS. 4I-4J) and rotation or translation of tube 34 against suture severing tube 28 (as shown by arrow in FIG. 6B) may cut the thread against a sharpened blade-like projection 30.

Insertion device 12 may further include a needle 36. Needle 36 may be positioned inside tube 34 or inside outer tube 22 or severing tube 28 and houses one or more anchoring elements 24 and thread 26. The anchoring elements may be separated by guide tube 46. Needle 36 may be located inside outer tube 22 such that a sharpened end 40 of needle 36 may be in proximity to outlet end 38 of outer tube 22 and one or more anchoring element 24 may be located inside needle 36. Needle 36 may be advanced distally within tube 22 (via handle 16) to penetrate the abdominal wall and/or a tissue and/or mesh and deliver anchoring element 24 and thread 26 therethrough. When handle 16 may be actuated, a plunger 37 (shown in FIG. 7A) may move forward (distally) and move anchor element 24 distally with or without ejection of anchoring element 24 out of needle 36. In an alternative embodiment, plunger 37 may move along with needle 36 and actuation of handle 16 retracts tissue piercing tube 36 to eject anchor 24.

In some embodiments, needle 36 may include at least one elongated slit 39 substantially parallel to the needle's central axis. The elongated slit (illustrated in FIGS. 2B and 2C) may be used to guide a fin element included in anchoring element 24. The slit 39 may be ended towards the shaft outlet 38 or at the shaft outlet. The fin element may protrude over the slit. The fin element is discussed in detailed below with respect to FIG. 3I.

Needle 36 may be fabricated from an alloy or polymer (e.g. stainless steel, cobalt chrome, Nitinol, PEEK, carbon, composite material, reinforced plastics, ceramics) with a length of 5 mm to 2000 mm an outer diameter (OD) of 0.25 mm to 20.05 mm and an internal diameter (ID) of 0.2 mm to 20 mm. Needle end 40 can be double beveled or pointed. Needle end 40 proximal part may be blunt for not cutting the thread. Plunger 37 can be fabricated from similar materials and lengths with an OD slightly smaller than an ID of tissue piercing tube 36.

The lumen of a distal end portion 40 of needle 36 may be configured to ensure that anchoring element 24 may tilted (with respect to the longitudinal axis of needle 36) when pushed out of needle 36 (via plunger 27 or by another embodiment via advancing assemble 45). Needle end 40 angle may enable the ejection of anchor element 24 tilted by forming an angle with respect to needle's 36 longitudinal axis. For example, the lumen of tube 36 can include a bump or 'ramp' or shaped with an angle to initiate tilt of anchor 24 as it exits the distal end of tube 36.

It will be appreciated that the tissue piercing function of needle 36 may also be provided by anchoring element 24 and/or outer tube 22. In some embodiments, anchoring element 24 may include a sharpened end for piercing the tissue at at least one of the anchoring element. As anchoring element 24 may be advanced within tube 22, a sharpened end thereof can be carried through the tissue by tube 22 and provide the through tissue path for tube 22 (and anchoring element 24 and thread 26 carried thereby).

Guide tube 46 may be fabricated from an alloy or polymer (e.g. stainless steel, cobalt chrome, Nitinol, PEEK, carbon, composite material, reinforced plastics, ceramics) and optionally coated (e.g. Teflon©) to enable smooth feeding of thread 26 into tube 46 therein and threading anchoring element 24 thereupon. Guide tube 46 may have a length of 5 mm to 2000 mm, an outer diameter (OD) of 0.1 mm to 20 mm and an internal diameter (ID) of 0 to 20 mm.

Guide tube 46 may serve to facilitate sliding of anchoring elements 24 thereupon and thread 26 therein. An anchoring element 24 threads directly over thread 26 once it is advanced off of tube 46.

Although guide tube 46 may be shown with a circular cross section, it will be appreciated that a guide tube 46 with a non-circular cross section (e.g. oval, square) can also be used herein. Use of such a guide tube 46 in device 12 included in apparatus 10 may be advantageous since it may be used to guide anchoring elements 24 (of similar cross sectional shape) in a predefined rotational direction thus ensuring that all anchors 24 exit tube 36 in the same rotational direction.

In some embodiments, insertion device 12 included in apparatus 10 may further include an advancing assembly 45, illustrated in FIGS. 2B-2C, for advancing one or more anchoring elements 24 along outer tube 22 towards the outlet end 38 of outer tube 22. In some embodiments, advancing assembly 45 may further be configured to cause anchoring element 24 exiting outer tube 22 from outlet end 38 to tilt in the tissue relative to the direction of longitudinal axis of outer tube 22. Advancing mechanism 45 may include a tilting mechanism 47 located in proximity to outlet end 38. Tilting mechanism 47 may include an elongated flexible pusher 49 to push anchoring element 26. Pusher 49 may be inserted via slit 39 of needle 36, thus bending while advancing element 26, causing element 26 to tilt. The tilting may start already while anchor is entering the proximal part of the needle sharp end 40 and continue after exiting the needle. For example, pusher 49 may be inserted into an edge or a fin element included in anchoring element 24. Advancing mechanism 45 may cause advancing of each anchoring element separately. Alternatively, advancing mechanism 45 may cause advancing of a plurality of anchoring elements simultaneously. Detailed disclosure of the tilting mechanism is given with respect to FIGS. 10E-10G. Advancing mechanism 45 may be operated and activated activating a trigger or by pushing a button in user interface 20 included in handle 16. Advancing mechanism distal end may have various shapes. In some embodiments, advancing mechanism 45 may push an anchor element 24 distally into the tissue more distant from the needle end, generating an axial distant from the anchor proximal end and the needle distal end causing the anchor to channel its own rout in the tissue.

In some embodiments, part or all of the tilting may occur while anchor element 24 progresses distally in the tissue while radial forces are applied causing the anchor element 24 to progress distally in a curved rout after the thread 26 is locked on the anchor 24 (pendulum effect) and/or when the advancing mechanism 45 pushes the anchor in the tissue in a curved rout and/or when suture arm or arms 52 may be pulled distally.

In some embodiment, locking of anchor element 24 in the tissue may be enhanced by the anchor rout or traveling. The needle 36 may penetrate the tissue wall axially. Anchor element 24 may be actuated by the handle 16 progress distally while in the needle 36. Once exiting needle 36 with or without tilted position, anchor 24 may progress in a curved out. Thus, tubes 22, 28, 34, needle 36, mechanism 45 and tube 46 provide the following functionality to insertion device 12 and the device may be manufactured with or without each of the following components:

(i) Outer tube 22 may support internal tubes 28, 34, needle 36 and 46; a distal end 38 thereof may be positionable against a tissue wall to enable device actuation in position and holding the thread against the mesh or tissue surface; outer tube 22 may be fixed in position.

(ii) Needle 36 may pierce through a tissue wall when advanced distally from handle 16 to enter the abdominal cavity or to deliver anchoring element 24 and thread 26 through the tissue. Advancing mechanism 45 may advance anchoring element 24 along needle 36 and/or outer tube 22. Sharpened end 40 of needle 36 is extendable out of opening 38 a predetermined distance as set by handle 16.

(iii) Tube 34 may hold thread 26 to enable a new anchoring element 24 delivering cycle over the suture. Thread severing tube 28 and tube 34 may cooperate to sever thread 26 and enable thread severing and holding prior to delivery of one or more anchoring elements 24; both tubes may advance out of tube 22; tube 34 with captured thread end may be aligned with, and rotated (or optionally translated) within tube 28 to sever suture.

(iv) Guide tube 46 serves to facilitate smooth advancement of both anchoring element 24 and thread 26.

As is mentioned herein, apparatus 10 and insertion device 12 may be used to deliver one or more anchoring element-thread loops through a tissue. Some exemplary embodiments of anchoring elements 24 with and without attached loop of thread 26 are shown in FIGS. 3A-3G.

An anchoring element according to embodiments of the invention may be anchored in the tissue and may further include a thread locking element which may lock thread 26 during or after insertion of the anchoring element to the tissue. A plurality of such anchoring elements may be consecutively inserted into the tissue to anchor and generate a running suture. Embodiments of anchoring element 24 may include a central elongated body 23 adapted to be threaded on a thread 26 and a locking element such as for example, at least one recess 50. Additional locking element different from recess 50 is discussed with respect to FIG. 3D. The locking element may be configured to lock thread 26 on anchoring element 24 during insertion of the anchor element. In some embodiments, recess 50 may have a wide end 51 and a narrow end 53. Narrow end 53 may grip thread 26 during anchoring. In some embodiments, anchoring element 24 may include a central elongated body 23 adapted to be threaded on a thread 26 and having a locking element, such as at least one of recess 50, slit, or the like.

Central elongated body 23 may substantially a hollow cylinder or tube and includes at least one, preferably 2 or 4 or more recesses 50 for trapping two 'arms' 52 of a suture loop 54 therein. Recesses 50 may include a tapered or sawtooth configuration or preferably, a slightly tapering rectangular shape having a wide end 51 and a narrow end 53 as is shown in FIG. 3C. Anchoring element 24 end portions may terminate in a blunt or sharpened end (for penetrating through tissue as described above). Anchoring element 24 may be fabricated from a biocompatible alloy or polymer such as PEEK or Absorbable Polymer (PGA, PLA PLGA) or the like. Anchoring element 24 may be biodegradable or not depending on use.

Alternative configurations of anchoring element 24 may utilize any thread-trapping elements which are 'activated' prior to release of anchoring element into tissue. Such configurations may include, for example, an element fabricated from a shape memory alloy (such as Nitinol) or any other elastic material (e.g. elastic polymer) that may be linearized when anchoring element 24 may positioned (threaded) on guide tube 46 and folds to form a shape that traps and engages thread 26 once released from guide tube 46. For example, FIG. 3D illustrates an anchoring element 24 which may include an exemplary locking element in the form of one or more deformable tabs 25 which deform inward to trap thread 26 once anchoring element 24 may be released from device 12. Tabs 25 may be maintained linear with anchoring element 24 body when anchoring element 24 may be positioned on tube 46 within insertion device 12. When released, anchoring element 24 may slide off tube 46 and tabs 25 bend inward to the position shown in FIG. 3D.

In any case, anchoring element 24 may be configured such that it is capable of sliding on thread 26 within outer tube 22 and locking thereagainst when delivered out of the distal end of apparatus 10.

As anchoring element 24 may slide off tube 46 (when anchor 24 advanced distally along suture 26 via handle 16), anchoring element 24 may thread directly over thread 26. Release of anchoring element 24 (threaded or not threaded over thread 26) on a far side of a tissue wall (from needle tube 36), may cause rotation and trapping (angular movement) of anchoring element 24. When suture arms 52 may be pulled against anchoring element 24 (abutting it against the far side of the delivery hole), suture arms 52 may slide into longitudinal recess 50 and are trapped therein thus forming the T-bar like configuration shown in FIGS. 3A-3B. As is further described herein below with respect to FIGS. 4A-4J, this formed T-bar like configuration may enables an anchoring 24 delivered through a tissue wall to abut the far side of the tissue hole with the suture arms positioned through the tissue hole.

Figure 3A:
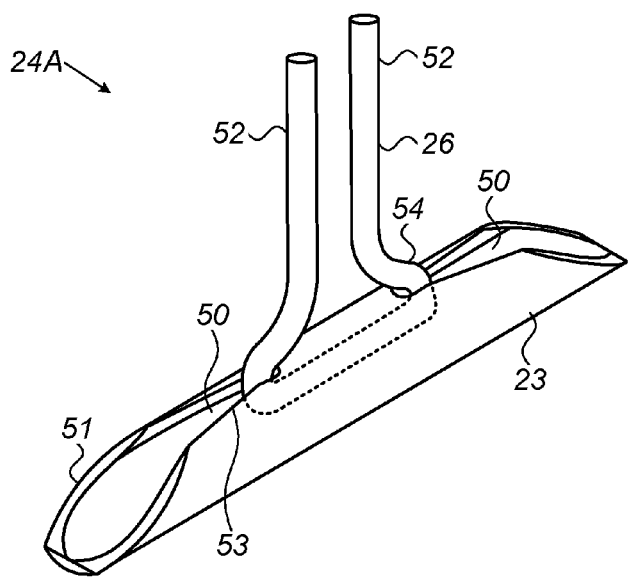
FIGS. 3A-3B are isometric illustrations of exemplary anchoring elements with a suture loop according to embodiments of the invention.
Figure 3B:
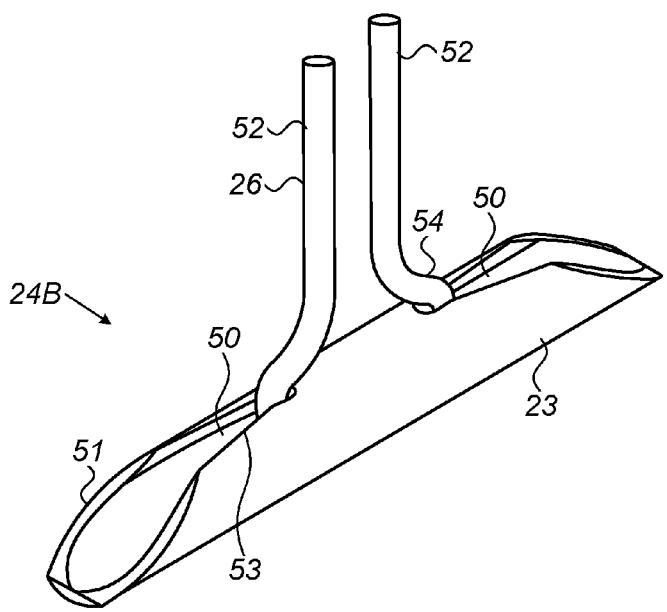
Figure 3C:
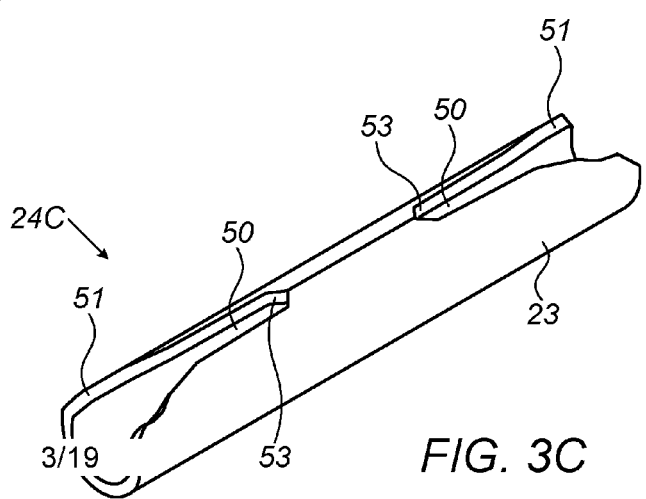
FIGS. 3C-3I are isometric illustrations of anchoring elements according to some embodiments of the invention.
Figure 3D:
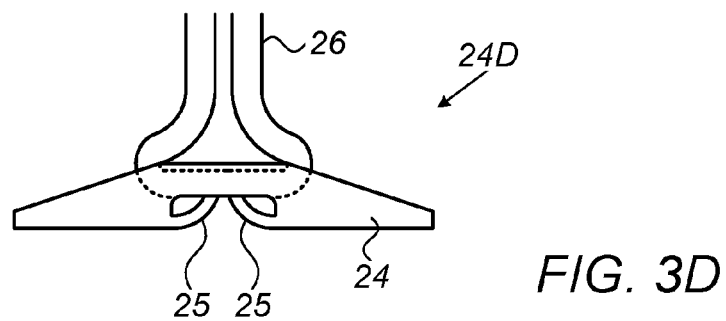
Figure 3E:
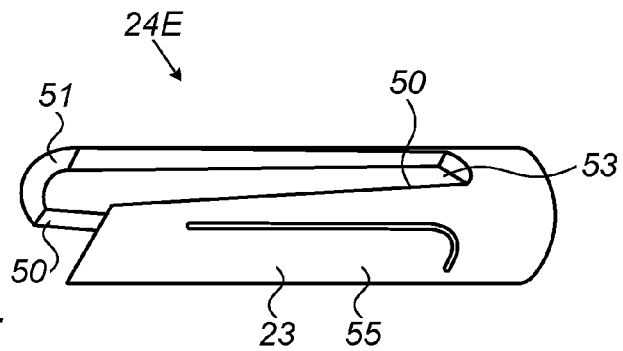
Figure 3F:
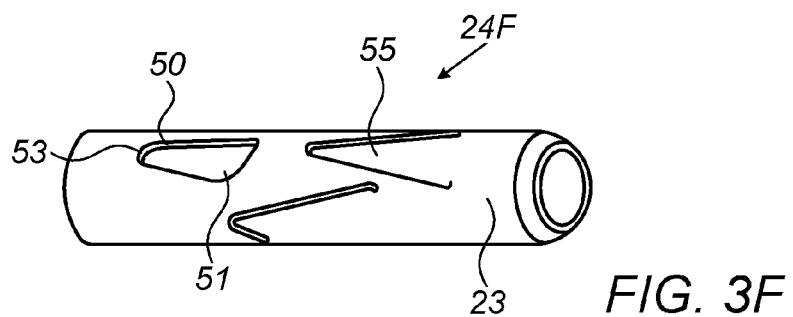
Figure 3G:
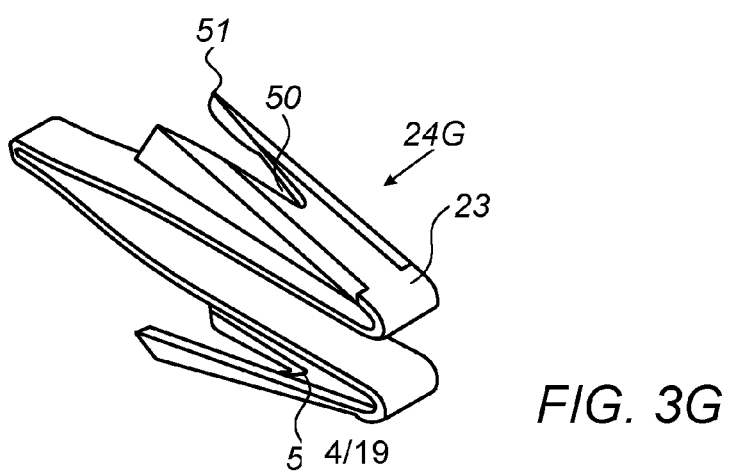

Additional exemplary anchoring elements 24E-24H are shown in FIGS. 3E-3H respectively. FIGS. 3E-3G are isometric illustrations of exemplary anchoring elements 24E-24G according to some embodiments of the invention. Embodiments of anchoring elements 24E-24F of FIGS. 3E and 3F may include central elongated body 23 having a form of a tube. In FIG. 3E two recesses 50 are located on two opposite peripheral sides (e.g., above and below) of the tubular body. Recesses 50 in FIG. 3E and also 3A-3D have wide end 51 of each recess 50 coincides with an end of the elongated body. In the embodiments of FIGS. 3A-3D length of each recess 50 may be shorter than half the length of the elongated body and/or the two recesses 50 may be symmetrically located from two ends of the elongated body. Embodiments of anchoring element 24F illustrated in FIG. 3f may include only one closed recess 50. Embodiments of anchoring element 24G of FIG. 3G may include an elongated body having a "spring shape". Such an element may or may not be configured to compress when inserted into outer tube 22 and extend when exit end 38 of insertion device 12. Element 24G of FIG. 3g may extend while anchoring threads 26 in the tissue, to further enhance the anchoring of the suture. In the exemplary embodiments of FIGS. 3A-3E and 3g two recesses 50 may have substantially the same shape. Alternatively, each of the two recesses may have a different shape. Anchoring elements 24E and 24G may not be threaded on guide tube 46 or thread 26 while in the insertion device 12. The locking of anchor elements 24E and 24G may occur when exiting the distal end 18 while thread 26 may be located in a contour shape on outer tube 22 outlet 38.

Figures 3H, 3I:
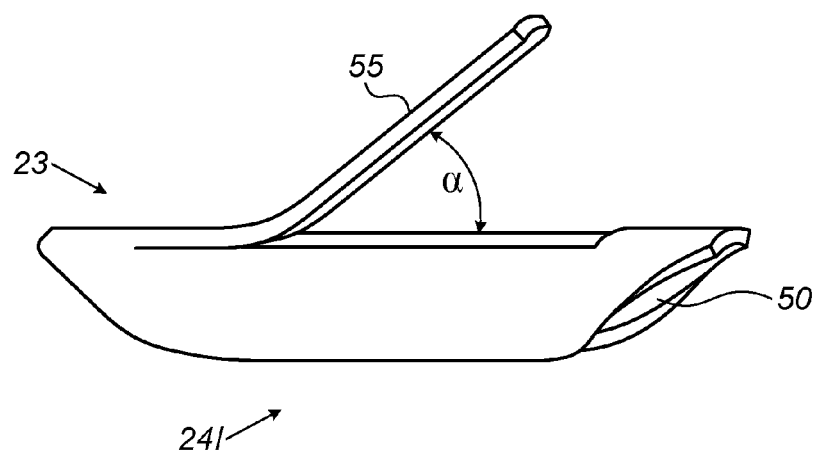

In some embodiments, anchoring elements 24, 24E-24F and 24H may further include a fin element 55, illustrated in FIGS. 3E-3F and 3H. Fin element 55 may have several functionalities. Fin 55 may by attached to advancing mechanism 45, such that elongated pusher 49 may push fin element 55 thus causing elements 24E-24F and 24H to advance forwarded in outer tube 22. Fin element 55 may slide inside elongated slit 39 in needle 36 (or a slit in any other tube included in device 12), thus ensuring that element 24 may always have the same orientation (prohibiting element 24 from rotating inside tube 22 or needle 36). When pushed out of insertion device 12, fin 55 may assist element 24 to tilt inside the tissue and avoid slipping back out of the tissue.

In some embodiments, fin element 55 illustrated in FIG. 3H may form an angle α (e.g., 90° or less) with the central elongated body 23 of anchoring elements 24. In some embodiments, fin element 55 may elastically bend towards the central elongated body (the bending may either have plastic or elastic features), for example when inserted into outer tube 22 or needle 36. In some embodiment the fin element 55 may be rigid. In some embodiments, anchoring element 24H may be threaded on guide tube 49 or guided otherwise inside insertion device 12. As anchoring element 24H may be positioned inside insertion device 12 a sharp angle α formed by fin elements 55 of anchoring element 24H may be facing inlet end (proximal portion) 14 (illustrated in FIG. 1) of outer tube 22 opposite to outlet end (distal portion) 18.

Reference is now made to FIG. 3I which is an illustration of an anchoring element according to some embodiments of the invention. An anchoring element 24I may include an elongated body 23 and a fin 55. Fin 55 may be configured to be lift up for sliding inside a slit in one of the tubes included in insertion device 12. Anchoring element 24I may have a proximal space past the fin to allow advancing assembly 45 to hold anchoring element 24I better on guide tube 34 and avoid its unwanted movements forward. This arrangement may stop anchoring element 24 from unintentionally (e.g., without being pushed) advancing further on the guide tube and to avoid accidental pushing of the element by the advancing assembly in the anchor's proximal part and not under the fin 55. Additionally, this configuration may further cause a better sliding of the anchoring element while keeping the fin open.

Embodiments of apparatus 10 may include a plurality of anchoring element 24 aligned in an insertion device 12, for example, in outer tube 22 or needle 36. Each of the anchoring elements may include locking element (e.g., a recess or a tab) to lock a thread 26. Insertion device 12 may be designed such that thread 26 may move freely within insertion device 12. After the insertion of anchoring elements 24 to a tissue each anchoring element may lock a portion of the thread to form a suture loop.

Anchor element 24 may have a locking element to lock the thread during or after the ejection of the anchor element. On one embodiment, the lock may occur while anchoring element 24 is pushed distally over the guide tube 46 or towards the shaft outlet end 38 or when suture arm or arms 52 are pulled to cause a tension FIGS. 4A-4J illustrate delivery of a single anchoring element 24 (with attached thread 26) from distal end 18 of apparatus 10.

Insertion device 12 may be positioned against the tissue thereby apparatus 10 in position. Actuation of handle 16 (or any other releasing device) may push (a pre-defined distance or several pre-defined distances) needle 36, plunger 37, (FIG. 7A) and/or advancing mechanism 45 (illustrated in FIG. 10) thus causing advancing mechanism 45 to push at least one anchor element 24 over the guide tube 46 and onto the thread; needle 36 (or alternatively, anchoring element 24 and/or outer tube 22 having sharpened end) may penetrate the tissue to a predefined depth. The same or a second actuation of handle 16 may push plunger 37 to advance anchor element 24 towards the distal end or needle 36 or outer shaft outlet 18 and push advancing assembly 45 to release anchoring element 24 from needle 36 and into the tissue. The thread may be tensioned and trapped against anchoring element 24 which may in turn rotated (e.g., tilt and curved rout) and trapped against the inner tissue surface. Thread 26 may be anchored in narrow side 53 of at least one recess 50. Handle 16 may be actuated again to distally push tube 34 thereby trapping thread 26 in slots 42 and to advance and/or rotate tube 28 thereby cutting thread 26. Alternatively, thread 26 can be severed and/or held using scissors and/or grasper thereby omitting the need for tubes 28 and 34.

Delivery of anchoring element 24 via the mechanism as described above is given as an example only, however, it will be appreciated that alternative delivery approaches which include rotation (torqueing) of anchoring element 24 into tissue or firing of anchoring element 24 into the tissue via, for example, a spring loaded firing mechanism are also contemplated herein.

FIG. 5A illustrate a continuous suture (running stitch) composed of five contiguous anchoring element-thread loops positioned using for example, apparatus 10, by repeating the steps outlined in FIGS. 4A-4H described above five times along a tissue 60. Each of the thread loops illustrated in FIG. 5A may be adjusted with different suture loop width or suture depth in the tissue. The arrows point at tissue holes 62 formed by needle 36. FIG. 5B is a magnified view of one anchoring element-thread loop. The thread length may be adjusted by the user based on tissue depth and tightness as well as distance between delivered anchor-suture loop. Anchoring elements 24 may abut in the tissue in any rotational orientation with the length of anchoring element 24 parallel to the tissue surface. Penetration into the tissue may be perpendicular or at any desired angle as long as anchoring element 24 may penetrate through the tissue wall and may be entrapped against its distal surface in any rotational angle.

FIG. 5C illustrates an example of a degradable (e.g. bio-absorbable) anchoring element 24 or semi degradable anchoring element 24 (fabricated from degradable and non-degradable portions) connected to a suture loop within tissue 60. Once anchoring element 24 degrades (partial degradation shown), the thread loop may maintain the shape and position shown due to tissue fibrosis around thread arms 52 and anchoring element 24 as well as fibrosis of tissue access site 62. Thus, following complete absorption of anchoring element 24, thread 26 may still provide the requisite fixation strength. In the case of a semi-degradable anchor, the non-degradable portion may further strengthen suture loop anchoring within tissue.

Following delivery of the anchor-suture loops, thread 26 can be cut as is illustrated in FIGS. 4I-4J and 6A-6B or by external scissors. Any number of anchoring element-thread loops (e.g. 1-100) may be placed through a tissue wall. Thread ends of a single anchor or a series of anchors may be tied or left untied.

As is mentioned hereinabove, actuation of tubes 28, 34, needle 36 and management of suture 26 may effected via a mechanism disposed in handle 16.

FIGS. 7A-7D illustrate an exemplary embodiment of an exemplary mechanism 70 which may be suitable for use with apparatus 10.

Figure 4A:
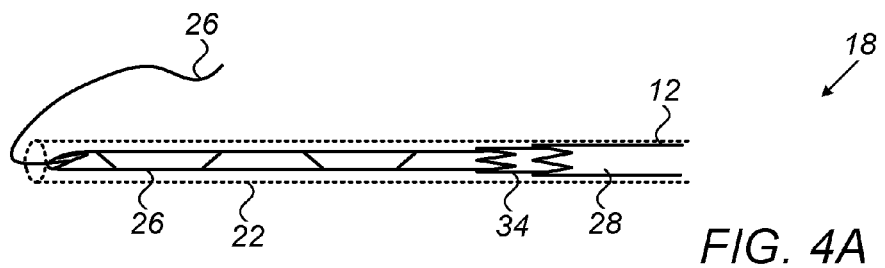
FIGS. 4A-4J are illustrations of several steps of the suture-delivery distal end of the apparatus of FIG. 1, according to some embodiments of the invention.
Figure 4B:
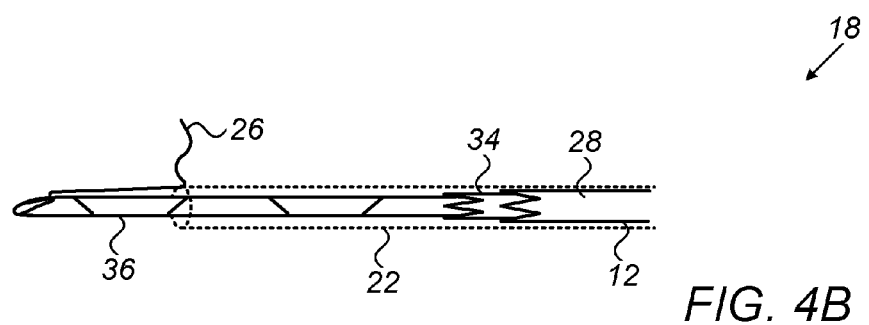
Figure 4C:
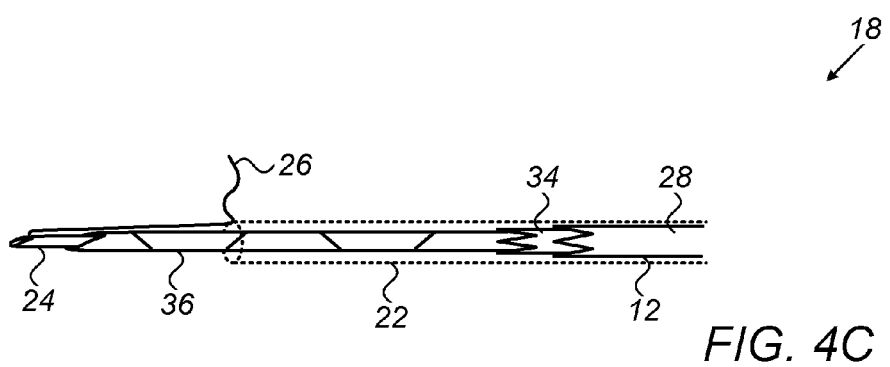
Figure 4D:
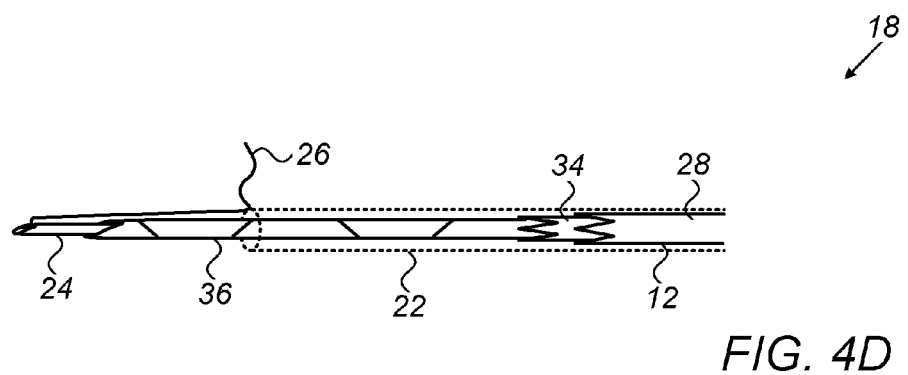
Figure 4E:
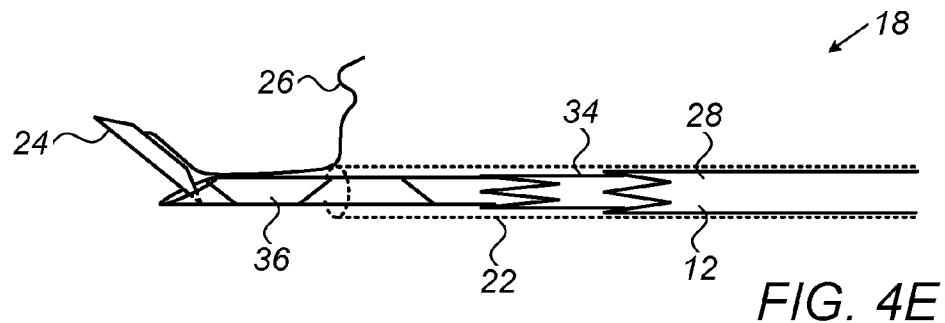
Figure 4F:
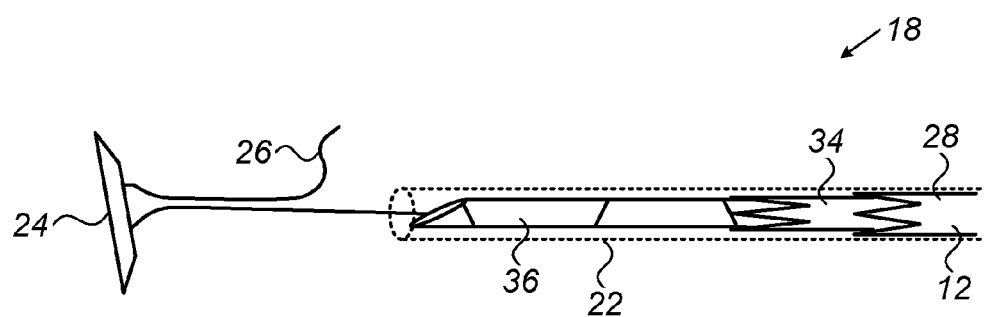
Figure 4G:
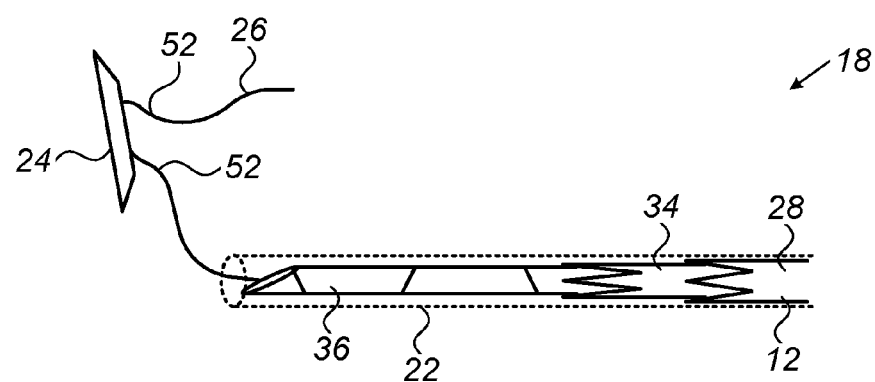
Figure 4H:
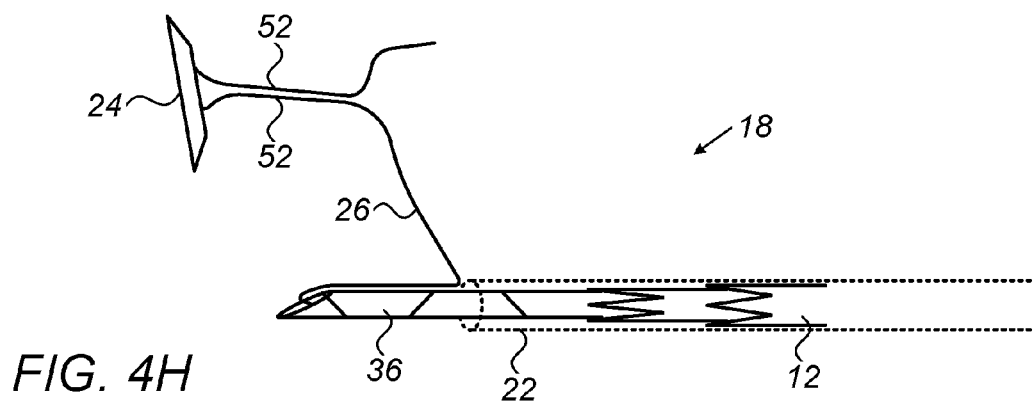
Figure 4I:
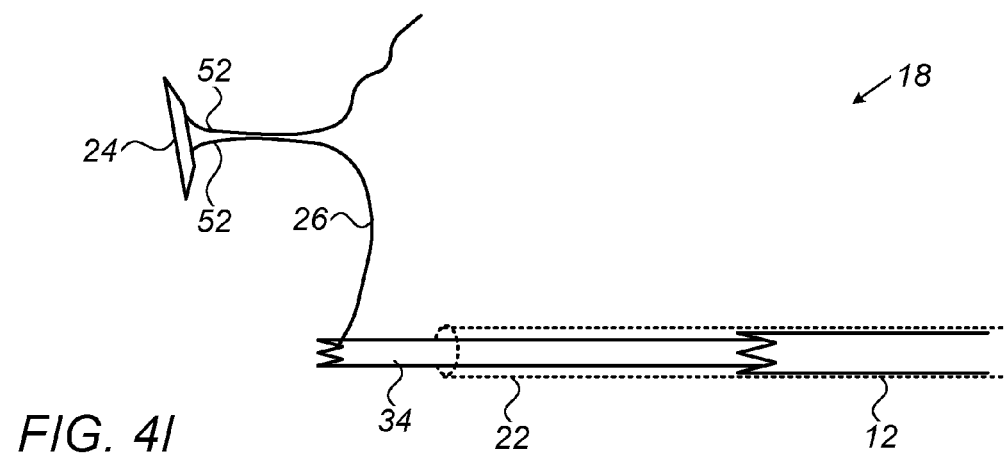
Figure 4J:
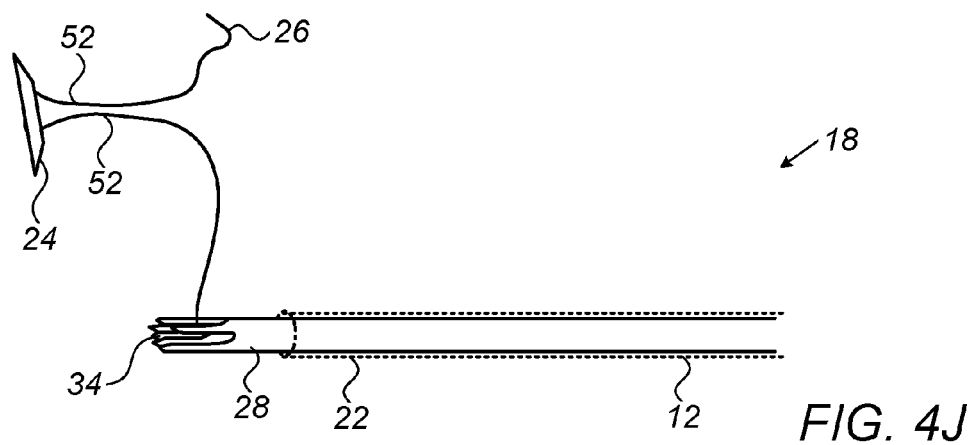

Actuation of trigger 70 may advance assembly 71 with respect to non-movable device 12 to pierce the tissue via needle 36 as is shown in FIGS. 4A-4B. The movement of assembly 71 may include simultaneous movements of assembly parts, device 12 does not move.

Figure 7A:
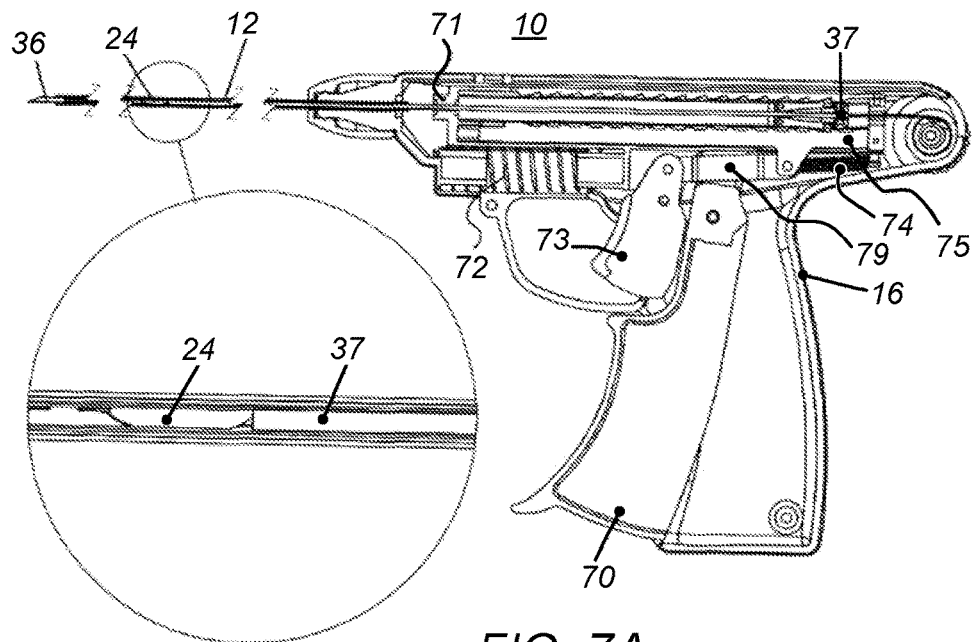
FIGS. 7A-7D are illustrations of a handle of the apparatus of FIG. 1, showing the anchoring element pusher mechanism and tissue piercing tube (FIG. 7A-7B) and the handle mechanism in normal mode (FIG. 7C) and actuated mode (FIG. 7D) according to some embodiments of the invention.
Figure 7B:
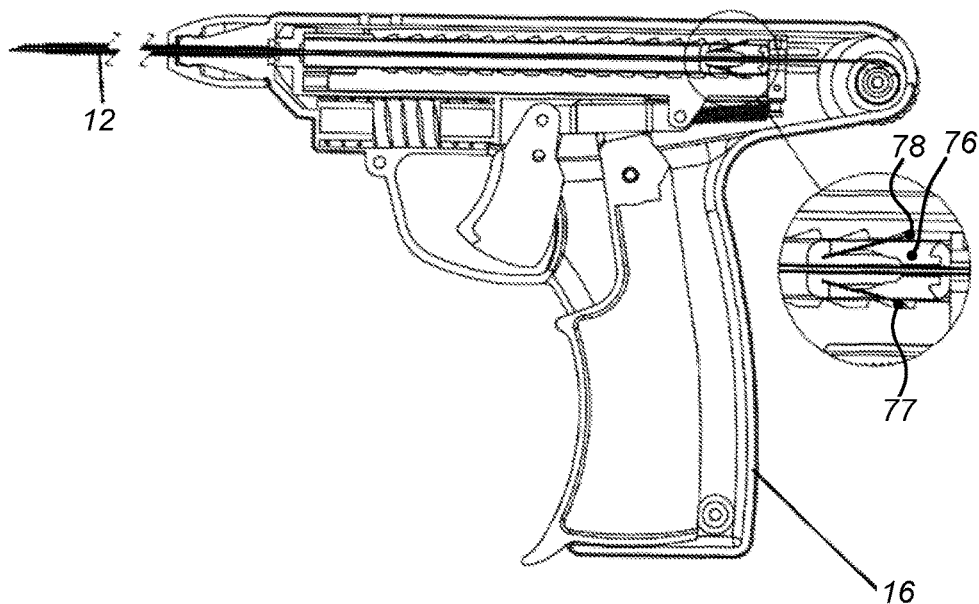
Figure 7C:
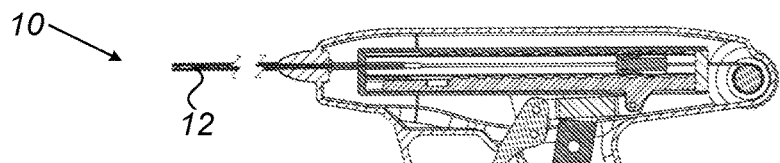
Figure 7D:
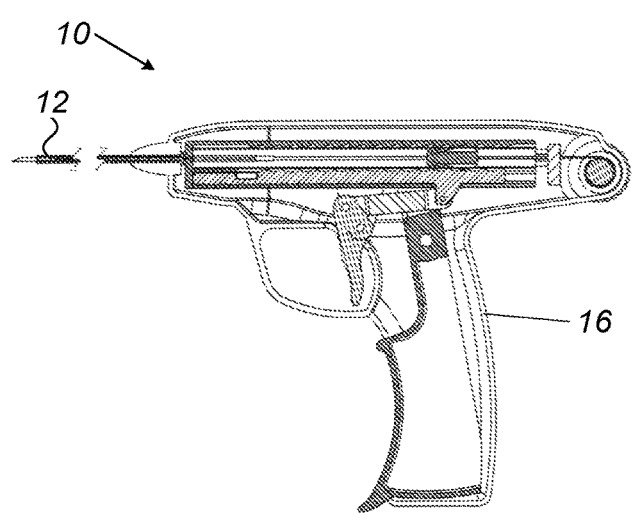

Spring 72 may be compressed as a result of forward movement of assembly 71. Actuation of trigger 73 may deliver an anchor-suture loop by pulling lever 79 that in turn may pull rack 75. One of the teeth in rack 75 may push leaf spring 77 distally which in turn may push element 76 (FIG. 7B). This may causes leaf spring 78 to skip a tooth of the serrated inner surface of assembly 71. This may prevent element 76 from going backwards when trigger 73 is released thus keeping the pusher in place and first (distal) anchor aligned with the distal end of tissue piercing tube 36. Actuation of trigger 73 may also compress spring 74 which may expand when trigger 73 is released to return rack 75 to its starting position with leaf spring 77 skipping a tooth in rack 75.

Release of trigger 70 may return apparatus 10 to its initial position to enable another cycle of tissue piercing and delivery of anchor-suture.

As is mentioned herein, apparatus 10 of the present invention can be used to fixate an implant to a tissue wall in a procedure such as hernia repair.

Laparoscopic hernia repair is an intra-abdominal, intraperitoneal repair that utilizes a mesh prosthesis to secure and cover a hernial defect; the hernia defect itself is usually not closed, though there are cases where the defect is suture or its contour is reduced. Traditionally, the mesh is anchored and held in position with trans-facial mattress sutures (2-0 or 0) provided at each corner of the repair. Typically, four mattress sutures are used, but for larger repairs eight or more mattress sutures are placed at 5 to 6 cm intervals. The sutures are tied subcutaneously through a small stab incision in the skin. In between the mattress sutures, the mesh is tacked or stapled to the abdominal wall fascia at 1 cm intervals with special hernia staples or spiral tacks.

In some embodiments, apparatus 10 may be used to repair an abdominal hernia as follows. A cannula may be positioned several centimeters away from the nearest border of the hernia, preferably at the midline. Pneumoperitoneum may established and an angled (30 or 45 degrees) laparoscope may be inserted to facilitate insertion of the other trocars. A single 5 mm or 10 mm trocar and optionally one or two 5 mm trocars or one or two three mm ports or percutaneous micro-laparoscopy tools may be positioned through the abdominal wall as far laterally as possible from the hernia. Next, grasping forceps and scissors may be used to reduce the hernia, and outline the defect in the fascia. For optimal exposure, the working ports may be positioned as far away from the hernia defect as possible. Since the mesh may overlap the defect by 3 to 4 cm, a very lateral or inferior position of the trocar site maximizes the view and efficiency of the procedure when the mesh is unrolled and deployed. Device 10 may be used to suture the defect or to reduce circumference of the defect The edge of the defect may be identified and marked on the skin and a piece of appropriately sized and tailored mesh prosthesis (with 3 to 5 cm cuff or margin lateral to the fascia defect in all directions) may be prepared and marked. The corners of the mesh may be marked to maintain the proper orientation when the mesh is sutured in place. The mesh may be inserted into the abdomen. The device 12 of apparatus 10 may be located above the hernia defect (outside the abdominal cavity) and may deliver at least one anchoring element 24 from the outside of the abdomen inside, passing the abdominal wall and the mesh. Fixating and/or adhering the mesh center and/or corners to the abdominal wall (from the inside) and in the right location where the hernia defect may be above the center of the mesh. At the end of the procedure, anchoring element 24 may be left behind or removed once the mesh is adhered and fixated. The apparatus 10 may be delivered preferably through a 10-5 mm port or a 2-3 mm incision or puncture (port-less) depending on the size and location of the hernia. The first corner of the mesh may be held using a grasper against the corner of the ventral defect. The distal tip of the present device may be pushed against the grasped mesh to penetrate the mesh and the tissue to a depth of 3-20 mm, depending on the thickness of the abdomen. Next, an anchoring element 24 may be delivered into the tissue as is described hereinabove. Apparatus 10 may then pulled back to tension the suture, lock it more firmly into the anchor and apply additional rotation to the anchor into its final position against the distal surface of the abdominal wall.

Apparatus 10 distal tip may be moved to the next desired location for fixation along with the extended length of suture and the suturing step may be repeated. Typically, 1-4 anchors may be deployed from the present device at each corner of the mesh (connecting thread may be left or cut after final fixation). Alternatively, the corner fixation may be performed with 2 or more consecutive anchor elements at each corner and the thread may be severed once moving from corner to corner. Once corner fixation is completed, the mesh is further fixated to the abdominal wall using apparatus 10 or standard approaches such as double crown or the like. Alternatively, the mesh may be initially fixated at its 4 four corners via standard trans-fasciae sutures or tacks and apparatus 10 may be used to perform additional fixation via single or running stitches. Alternatively, the suturing can be performed without fixation of the corners. The fixation of the mesh and advancing with the mesh fixation may be performed in any routinely order with one or more single or continuous stitches. Following fixation, the present device is removed from the abdomen and the access sites may be closed using apparatus 10 or any other approach known in the art.

Thus, the present invention may provide a tissue suturing device which may be used to approximate ligate and/or fixate tissue via open or minimally invasive procedures. Apparatus 10 may be used in ventral, umbilical, inguinal, or hiatal hernia repair, fundoplication, bariatric surgery via gastric sleeve, rectopexy and mesh or mesh-less assisted pelvic organ prolapse fixation, hysterectomy, myomectomy, abdominoplasty, mamopexy, rhytidectomy, meniscus repair or rotators cuff repair access site closure or any procedure which requires tissue to tissue or tissue to implant approximation/fixation or tissue/organ/device/implant lifting or holding or retracting.

Insertion device 12 of apparatus 10 may include a distal marker to ensure that the outer tube does not penetrate into the tissue, while needle 36 may include graduation marks to determine manual or one or more predefined depth of penetration. Additional markers may be positioned on outer tube 22 or tube 24 to enable visualization through imaging modalities or camera or to ensure that the device does not penetrate into the external tissue (e.g. the abdominal wall). Additional markers may be positioned on handle 16 indication the number of anchor elements 24 left in device 10.

The invention may provide several distinct advantages over currently available tissue suture/ligation/fixation approaches:

(i) the apparatus 10 may be used to produce a single tissue fixation point or multiple contiguous fixation points easily and rapidly with no need for additional knot tying in any type of tissue including a bone;

(ii) tissue/implant is sutured/fixated/ligated via a thread thereby providing a robust and reliable connection;

(iii) delivery of a suture loop may do not require access to the far side of a tissue wall;

(iv) delivery of suture may be adjusted for tissue thickness on the fly, enabling continuous suturing of varying thickness tissues;

(v) force of ligation may evenly distribute between contiguous suture loops thereby minimizing the likelihood of tissue ischemia;

(vi) apparatus 10 may be used with permanent thread/anchoring element or biodegradable thread and/or anchoring element;

(vii) apparatus 10 may penetrate the tissue vertically or at any selected angle;

(viii) the anchoring element may not protrude above surface minimizing tissue adherence or perforations;

(ix) the suture covers more surface thus reducing the number tacks/anchoring elements/sutures needed and the risk of damaging tissue such as blood vessels, nerves etc.;

(x) apparatus 10 may be used with a mini-port or delivered directly through the tissue (port-less) thus reducing the risk of infections and scarring; and (xii) apparatus 10 insertion device may be flexible and articulated and thus the device working head (tip) may be easily positioned within anatomically confined spaces.

(xiii) apparatus 10 may be delivered over a guide wire positioned within vascular tissue.

apparatus 10 may be used with a robotic surgical system which may actuate the device 10

Figure 7E:
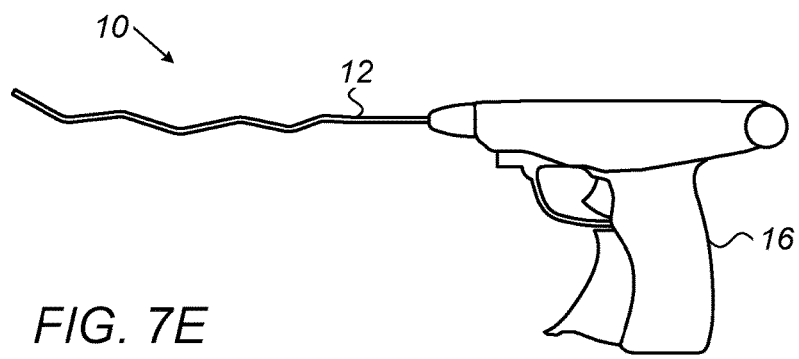
FIGS. 7E-7F are illustrations of the apparatus of FIG. 1 with a flexible insertion device (FIG. 7E) or deflectable insertion device (FIG. 7F) according to some embodiments of the invention.
Figure 7F:
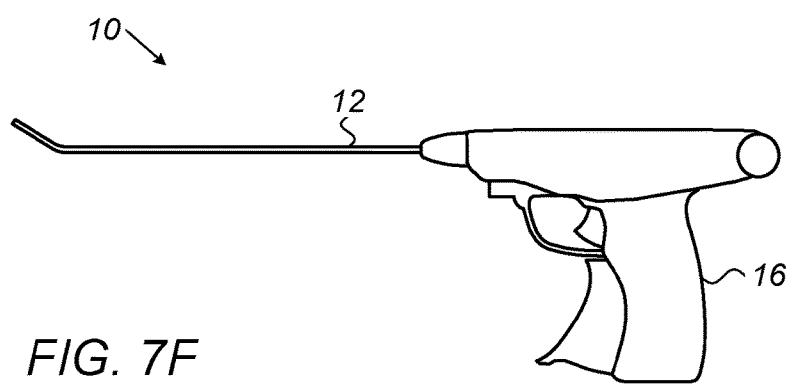

FIGS. 7E-7F illustrate embodiments of apparatus 10 having a flexible (FIG. 7E) or deflectable (FIG. 7F) insertion device 12 or curved towards shaft distal end 18. Such apparatus 10 configurations can be used in endoscopic or laparoscopic procedures. The tubes of flexible device 12 may be fabricated from an alloy or a polymer and may be elastically or plastically bendable. Device 12 may be constructed from a series of interconnected links or from a slotted tube(s). Control wires may run the length of the shaft and enable deflection of device 12 from the handle. Apparatus 10 may also include more than one devices 12 attached to a single handle 16. For example, a dual device 12 operable via a single handle 16 mechanism may be used to lay down a double suture line with simultaneously delivery of two anchoring elements a predetermined distance from each other. The devices may run parallel to each other or at a converged/divergent angles. In such a multi insertion device configuration, anchoring elements 24 can be connected in pairs, enabling release of one thread loop attached to two anchoring elements with every cycle. In such a configuration, the pair of anchors may be connected and the thread trapping mechanism following release may be optional.

Apparatus 10 may be fabricated using approaches well known in the art. For example, insertion device 12 and the tubes contained therein can be extruded or rolled from an alloy, while handle 16 can be fabricated from injection molded and machined components.

As used herein the term "about" refers to ±10%.

Additional objects, advantages, and novel features of the present invention will become apparent to one ordinarily skilled in the art upon examination of the following examples, which are not intended to be limiting.

EXAMPLES

Reference is now made to the following examples, which together with the above descriptions, illustrate the invention in a non-limiting fashion.

Example 1

Prototype Bench Testing 1

Initial experiments were performed with a prototype that includes the anchoring elements 24, threads 26 and insertion device 12 in order to determine feasibility of delivering an anchored suture through excised tissue. A 0.8 mm O.D. hollow alloy 8 mm in length was curved at the tips to form a groove for locking the suture. The tube was also tapered at the ends to facilitate penetration through a tissue access site. Ten individual anchoring elements were threaded over a 2-0 silk thread and the thread with threaded anchors was inserted into a 10 cm long hollow needle with a sharp tapered distal end capable of tissue piercing. A rod was fitted into the needle through the proximal end to serve as a plunger for expulsion of a suture anchor.

A standard 4×4 cm poly-propylene mesh was used along with a 20×20 cm piece of bovine abdominal muscle as the tissue model. The mesh was placed over the tissue and the needle was inserted through the mesh and into the tissue (to a depth of about 3 cm). The plunger was then advanced within the needle (about 1 cm) thereby pushing one anchoring element out of the needle and into the tissue. The pusher and needle were retracted out of the tissue, leaving a loop of thread and a threaded anchoring element over it, in the tissue. The process of anchoring element-thread delivery was repeated several times.

Example 2

Prototype Bench Testing 2

Figure 8A:
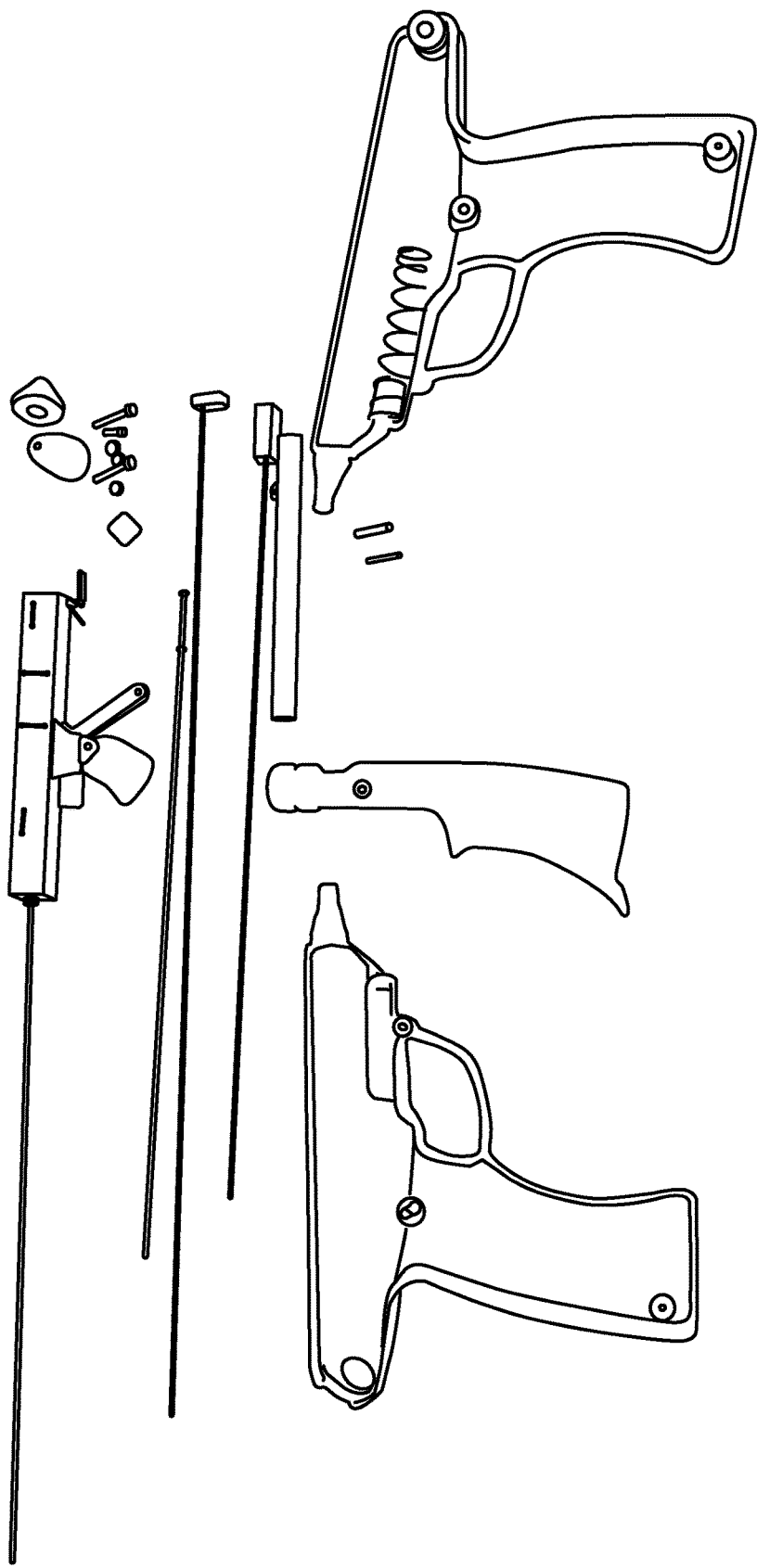
FIG. 8A depicts photographs of components useable for assembling an apparatus according to some embodiments of the invention.

A second prototype including handle was fabricated by 3D printing the handle and actuating mechanism and attaching it to concentrically arranged tubes (FIG. 8A). The prototype was tested by sequentially delivering several anchoring elements through a 3 cm thick foam board forming a running stitch (FIG. 8B-8C). The prototype was then used to deliver two anchoring elements (each with attached suture loop) through fascia of excised bovine muscle tissue to simulate fascia anchoring (FIG. 9A). The load capacity of a single anchor point exceeded 600 grams (FIG. 9B).

Figure 10A:
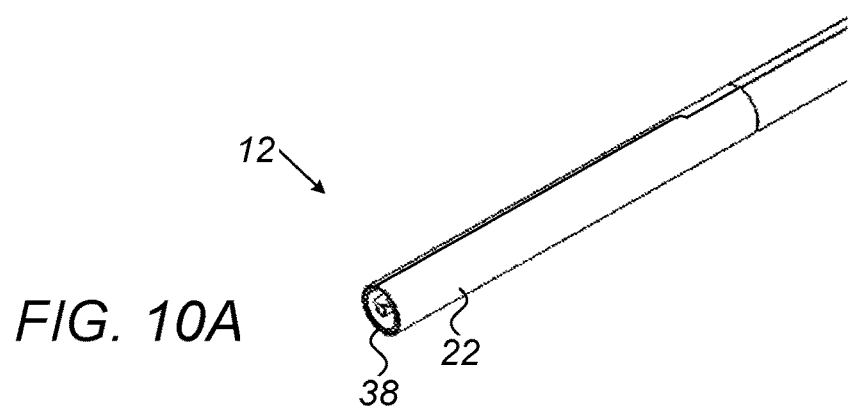
FIGS. 10A-10H are illustrations of various steps in the delivery or insertion of an anchoring element into a tissue using the device of FIGS. 2A-2C, according to some embodiments of the invention.
Figure 10B:
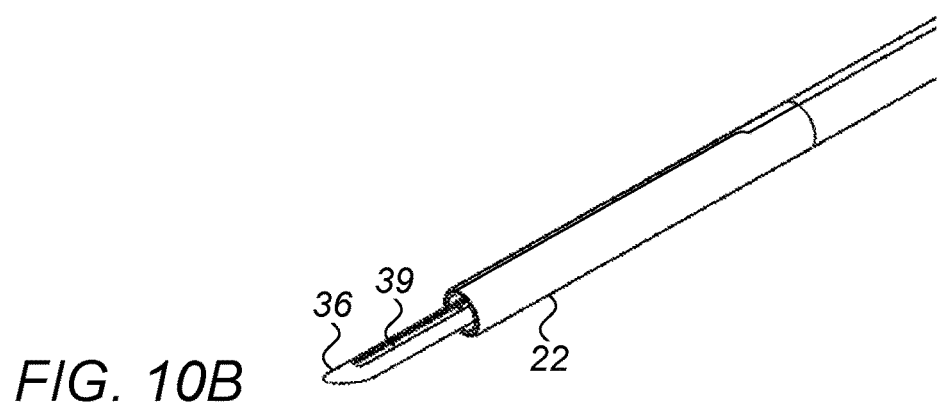
Figure 10C:
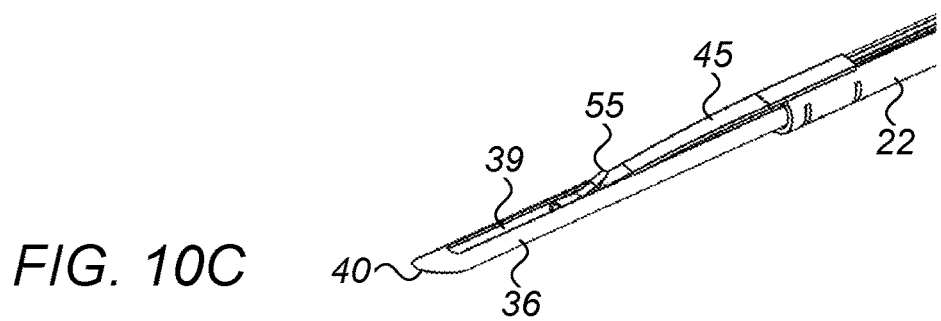
Figure 10D:
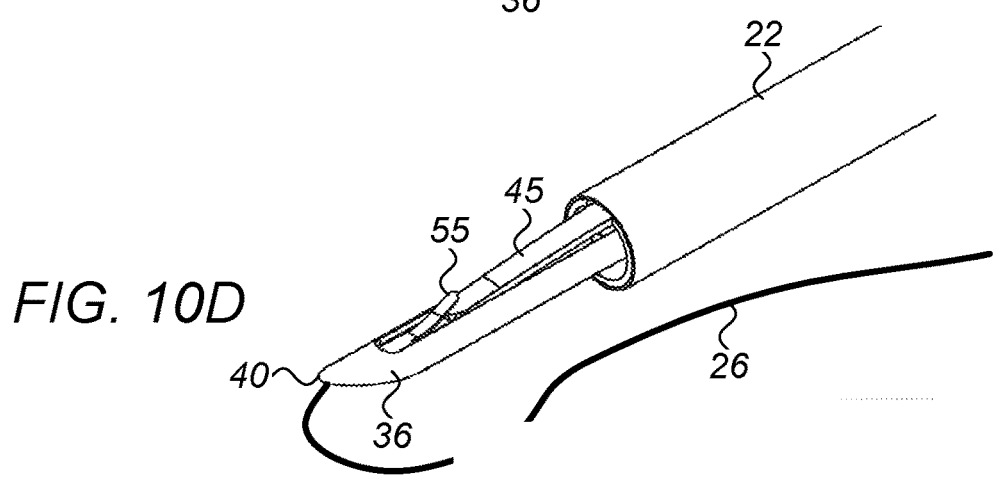

Reference is now made to FIGS. 10A-10H which are illustrations of apparatus 10 in several positions illustrating 8 steps in the insertion and/or delivery of a single anchoring element 24 using insertion device 12. FIGS. 10A-10H shows the advancing and positioning of the various elements of apparatus 10 (with respect to each other), discussed and disclosed above during the insertion of insertion device 12 and the delivery of anchoring element 24 and thread 26 into the tissue. During the insertion of anchoring element 24 by insertion device 12, element 24 may exit in tilt position from needle sharp end 40 and continue to tilt in the tissue as illustrated in FIGS. 10E-10H and discussed below with respect to the method of FIG. 12. FIGS. 11A-11B are illustrations of device 12 in two positions of performing delivery of a first anchoring element from a plurality of anchoring element inserted into device 12.

Figure 12:
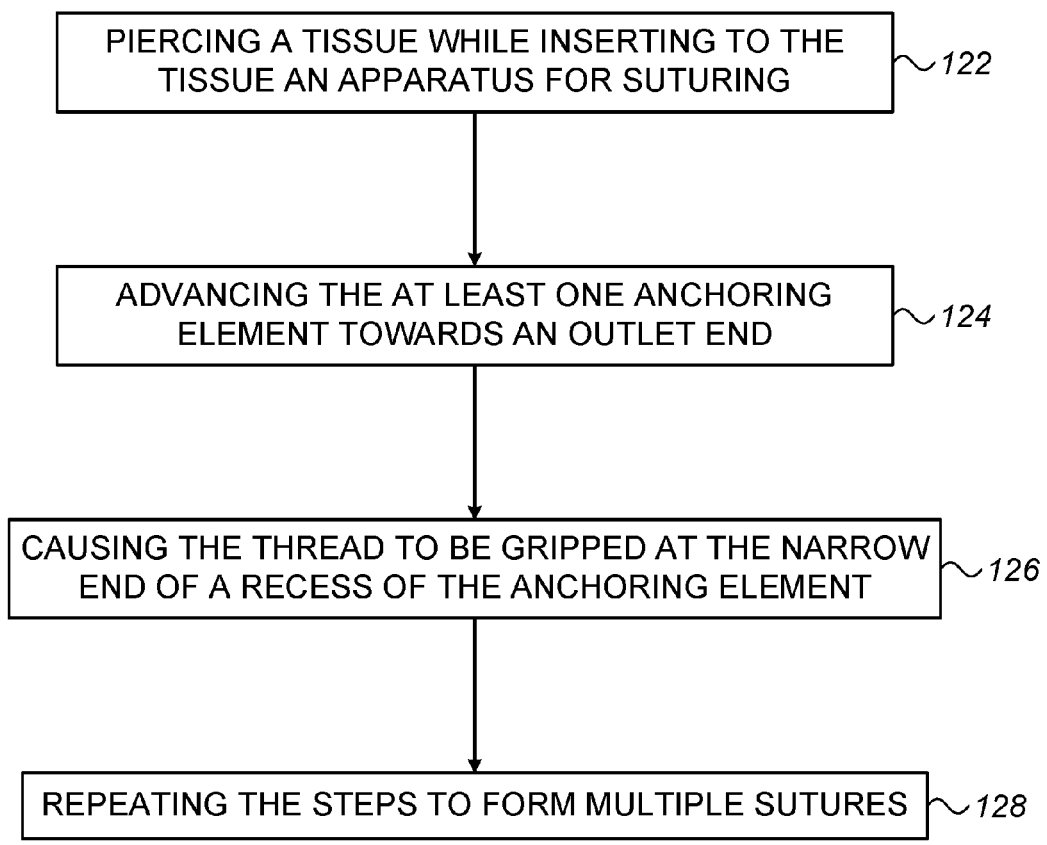
FIG. 12 is a flowchart of a method of suturing a tissue according to some embodiments of the invention.

Reference is made now to FIG. 12 which is a flowchart of a method of suturing a tissue according to some embodiments of the invention. In step 122, method according to embodiments of the present invention may include piercing the tissue while inserting to the tissue an apparatus for suturing, for example, apparatus 10. Apparatus 10 may include an outer tube 22, a thread 26 at least partially inserted inside outer tube 22 and at least one anchoring element 24. In some embodiments, apparatus 10 may further include needle 36 for piecing the tissue. In order to pierce the tissue needle 36 may be extend beyond end 38 of outer tube 22. Needle 36 sharpened end 40 may pierce the tissue, as illustrated in FIGS. 10A-10C. Alternatively, outer tube 22, guide tube 46 or anchoring element 24 may have a sharpened end for piercing the tissue.

Figure 10E:
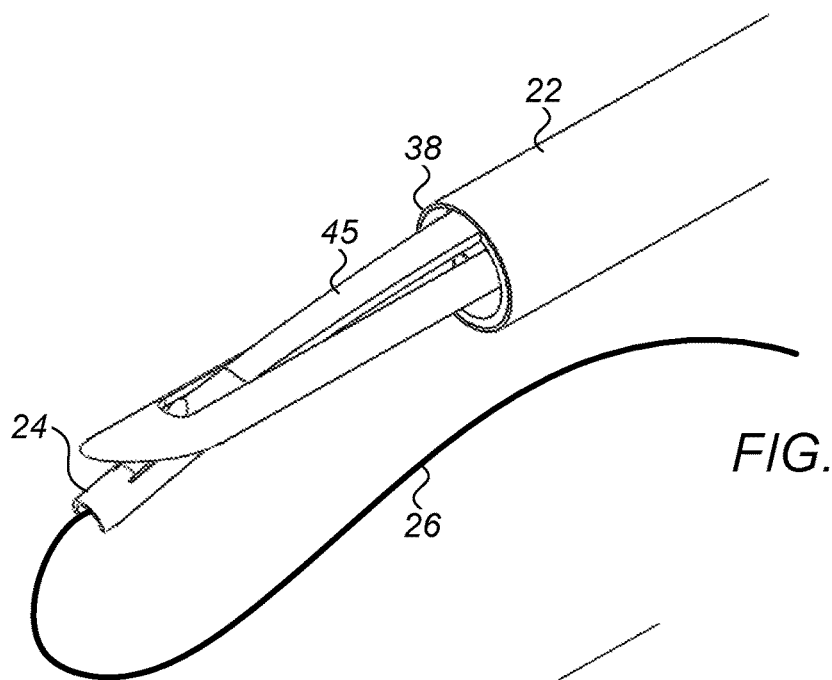
Figure 10F:
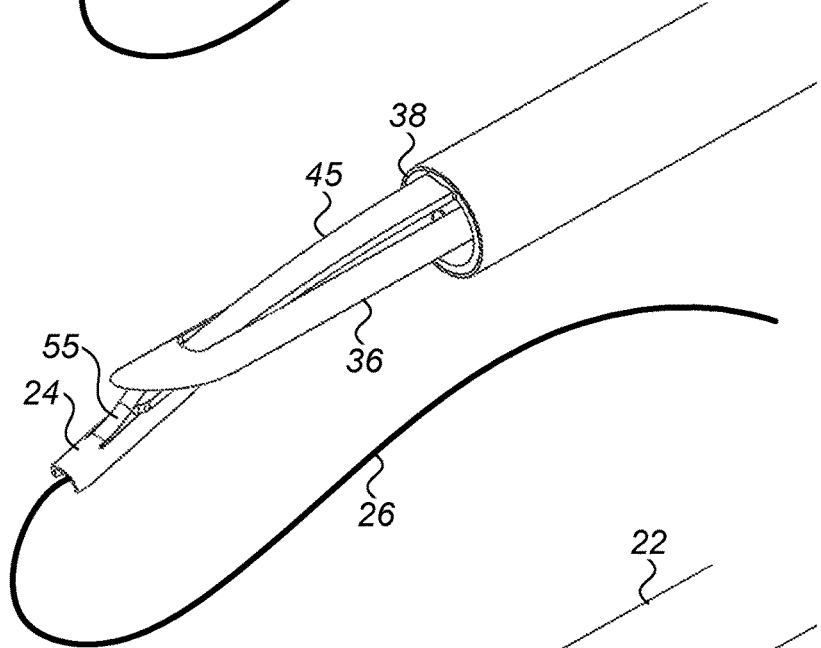
Figure 10G:
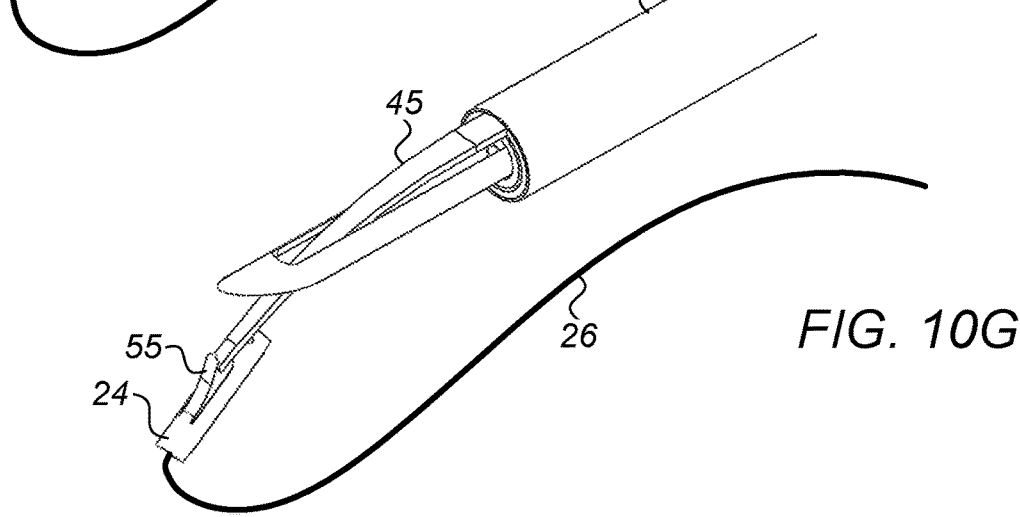
Figure 10H:
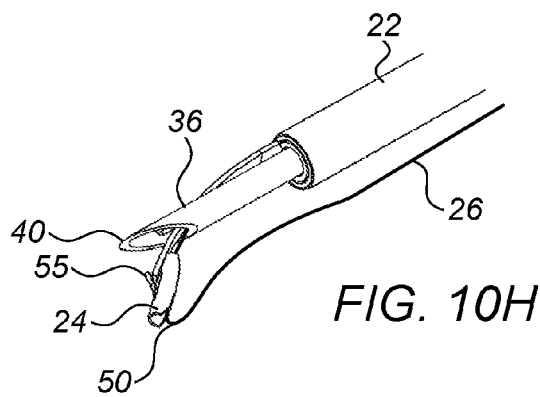
Figure 11A:
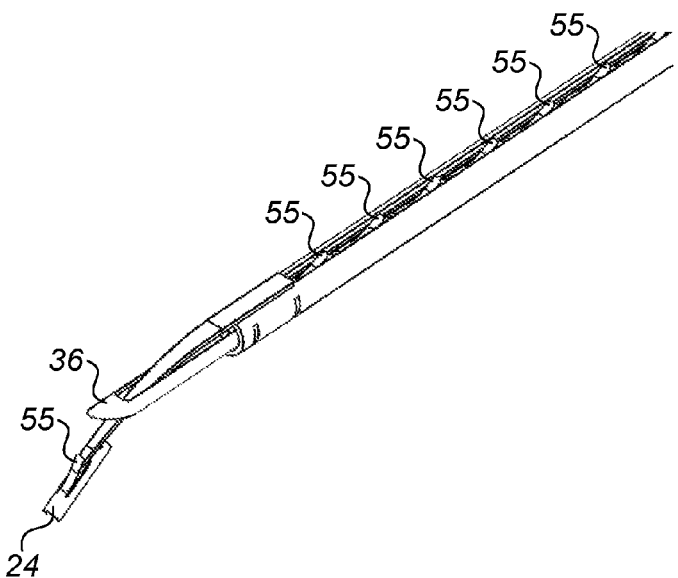
FIGS. 11A-11B are illustrations of a device for suturing a tissue comprising a plurality of anchoring elements according to some embodiments of the invention.
Figure 11B:
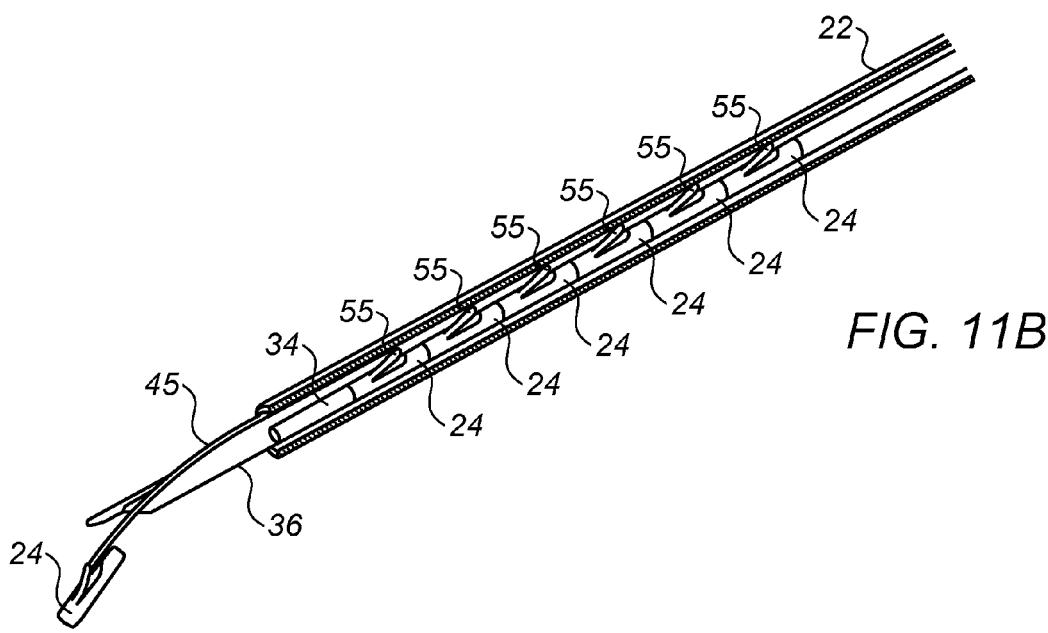

In step 124, embodiments of the method may include advancing at least one anchoring element 24 towards outlet end 38 of outer tube 22 to cause at least one anchoring element 24 to exit from outlet end 38 of outer tube 22 into the tissue such that at least one anchoring element 24 is anchored in the tissue and threaded on thread 26, as illustrated in FIGS. 10E-10F. In an exemplary embodiment, advancing mechanism 45 may push fin element 55 of anchoring element 24 along the longitudinal axis of insertion device 12. As illustrated in FIGS. 11A-11B a plurality of anchoring elements may be inserted into insertion device 12 one after the other. Advancing mechanism (e.g., pusher 49) may push each of elements 24 separately, for example, by pushing fin element 55. Alternatively, advancing mechanism 45 may advance two or more anchoring elements simultaneously.

Fin element 55 of each anchoring element 24 may slide inside an elongated slit included in one of the elongated components of insertion device 12. For example, fin element 55 may slide in slit 39 included in needle 36 (as illustrated in FIGS. 10A-10H). Alternatively, fine element 55 may slide inside a slit formed on outer tube 22, trapping tube 34, cutting tube 28 or guiding tube 46 (illustrated in FIGS. 2A-2C).

In some embodiments, advancing at least one anchoring element 24 towards outlet end 38 may include tilting at least one anchoring element 24 upon exiting outer tube 22, with respect to the longitudinal axis of outer tube 22. As can be seen in FIGS. 10E-10F, pusher 49 may be flexible and may bend when exiting from end 38 via slit 39 in needle 36. This bending may cause or help anchoring element 24 to tilt inside the tissue. In some embodiments, anchoring element 24 may continue to tilt in the tissue and advance in a curved rout after exiting insertion device 12. Additional tilting may be caused by pulling the portion of thread arm 52. In some embodiments, when tilted anchoring element 24 may move in a curved rout in the tissue.

In step 126, the method may include causing thread 26 to be gripped by the locking element, for example, at narrow end 53 of recess 50, or by tabs 25 included in anchoring element 24, as illustrated in FIGS. 3A-3B. In some embodiments, anchoring element 24 may include at least one recess 50 and thus, when manipulating thread 26 may cause thread to be gripped at narrow end 51 of recess 50 of the anchoring element.

Handle 16 may activate advancing mechanism 45 by, for example, pushing a button or a trigger in user interface 20.

In some embodiments, the method may include pulling apparatus 10, by pulling insertion device 12, from the tissue such that thread 24 may be anchored in the tissue by at least one anchoring element 24, as shown in the photographs of FIGS. 8B and 9A.

In some embodiments, the method may further include causing anchor element 24 to be anchored in the tissue, for example, by puling thread 26.

In step 128, the method may include repeating operation 122-126, to form a plurality of sutures, also known in the art as running stitch. Such an embodiment was disclosed above with respect to FIG. 5A.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. An apparatus for suturing tissue, comprising:
   (a) an elongated shaft;
   (b) a needle disposed inside said elongated shaft such that a sharp end of the needle is in proximity to a distal end of said elongated shaft, wherein said needle is advanceable distally within said elongated shaft, to penetrate the tissue, and wherein said needle has an elongated slit substantially parallel to a central axis of said needle;
   (c) a handle disposed at a proximal end of said elongated shaft;
   (d) a thread disposed along the length of said elongated shaft;
   (e) multiple anchoring elements:
      disposed inside said needle, along the length of said needle,
      threaded on said thread, and
      each of said anchoring elements comprising:
         a tubular elongated body through which said thread is threaded,
         a first longitudinal recess in a first peripheral side of said body, wherein said first longitudinal recess is tapered and has a narrow end and a wide end, the wide end coinciding with an end of said body, and
         a fin extending away from said body at a sharp angle with respect to said body, wherein said fin is configured at least to prevent the anchoring element from slipping back, out of the tissue, and wherein said fin is configured to lift up and slide inside said elongated slit of said needle; and
   (f) an advancement mechanism triggerable by said handle and being configured to:
      consecutively eject said anchoring elements out of the distal end of said elongated shaft and into the tissue, by pushing the fin of each of said anchoring elements, and
      tilt each of the ejected anchoring elements by continuing to push the fin of the ejected anchoring element after the anchoring element is ejected out of the distal end of said elongated shaft,
      wherein the ejecting and the tilting form a continuous suture composed of said thread anchored to the tissue by a plurality of said anchoring elements that are each locked to said thread by said narrow end of said first longitudinal recess gripping said thread,
      wherein said advancement mechanism is a flexible pusher configured to exit an outlet end of said needle via said elongated slit of said needle, thereby bending said flexible pusher and pushing each of said anchor elements in a curved route through the tissue.

2. The apparatus according to claim 1, wherein said advancement mechanism is further configured, by said tilting, to cause said thread to slide into said narrow end of said first longitudinal recess.

3. The apparatus according to claim 1, wherein said continuous suture comprises multiple T-bars, each formed of one of said tilted anchoring elements and two strands of said thread that extend from two sides of said one of said anchoring elements.

4. The apparatus according to claim 1, wherein said thread is freely accommodated inside said multiple anchoring elements, such that said multiple anchoring elements can slide along the length of said elongated shaft.

5. The apparatus according to claim 1, wherein said elongated shaft has a sharp distal end for piercing the tissue.

6. The apparatus according to claim 1, wherein said handle comprises a control for setting a depth of tissue penetration by said needle.

7. The apparatus according to claim 1, wherein said handle comprises controls for:
   setting a depth of tissue penetration;
   actuating tissue piercing;
   generating tension on said thread;
   triggering said advancement mechanism; and
   severing said thread at the end of a suturing cycle.

8. The apparatus according to claim 1, further comprising a thread severing tube and a thread trapping tube that are disposed inside said elongated shaft and are configured to cut said thread by rotation.

9. The apparatus according to claim 1, wherein each of said multiple anchoring elements is made of an alloy.

* * * * *